United States Patent
Bowden et al.

(10) Patent No.: US 8,563,254 B2
(45) Date of Patent: Oct. 22, 2013

(54) BIOMARKERS OF TUMOR PHARMACODYNAMIC RESPONSE

(75) Inventors: Michaela Bowden, County Limerick (IE); Alan Buckler, Arlington, MA (US); Chantale T. Guy, Medford, MA (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 12/905,273

(22) Filed: Oct. 15, 2010

(65) Prior Publication Data

US 2011/0092508 A1 Apr. 21, 2011

Related U.S. Application Data

(60) Provisional application No. 61/252,497, filed on Oct. 16, 2009.

(51) Int. Cl.
*G01N 33/53* (2006.01)
*A61K 31/16* (2006.01)

(52) U.S. Cl.
USPC .......................................... 435/7.1; 514/613

(58) Field of Classification Search
None
See application file for complete search history.

(56) References Cited

FOREIGN PATENT DOCUMENTS

| WO | 9700601 A2 | 1/1997 |
|---|---|---|
| WO | 9700893 A1 | 1/1997 |
| WO | 2004072051 A1 | 8/2004 |

OTHER PUBLICATIONS

Jensen et al., "NVP-AUY922: a small molecule HSP90 inhibitor with potent antitumor activity in preclinical breast cancer models," Breast Cancer Research 10(2):1-12 (2008).
Eccles et al., "NVP-AUY922: a Novel Heat Shock Protein 90 Inhibitor Active Against Xenograft Tumor Growth, Angiogenesis, and Metastasis," Cancer Research 68(8):2850-2860 (Apr. 15, 2008).
Christensen et al., "Plasma vascular endothelial growth factor and interleukin-9 as biomarkers of antitumor efficacy of a prototypical erbB family tyrosine kinase inhibitor," Molecular Cancer Therapeutics 4(6):938-947 (Jun. 1, 2005).
Crawford et al., "A novel B-RAF inhibitor blocks interleukin-8 (IL-8) synthesis in human melanoma xenografts, revealing IL-8 as a potential pharmacodynamic biomarker," Molecular Cancer Therapeutics 7(3):492-499 (Mar. 1, 2008).

*Primary Examiner* — Prema Mertz
(74) *Attorney, Agent, or Firm* — Paul J. Paglierani

(57) ABSTRACT

The present invention provides novel biomarkers, and methods of using said biomarkers, for assessing the efficacy of a treatment regimen for treating cancer in a subject, particularly for treating cancer via Hsp90 inhibition. The present invention also provides methods of identifying test agents capable of treating cancer, particularly in the case of cancers characterized by high levels of IL-8.

1 Claim, 6 Drawing Sheets

SEQUENCE LISTING

<160> NUMBER OF SEQ ID NOS: 5

<210> SEQ ID NO 1
<211> LENGTH: 99
<212> TYPE: PRT
<213> ORGANISM: Homo sapiens

<400> SEQUENCE: 1

Met Thr Ser Lys Leu Ala Val Ala Leu Leu Ala Ala Phe Leu Ile Ser
 1               5                  10                  15

Ala Ala Leu Cys Glu Gly Ala Val Leu Pro Arg Ser Ala Lys Glu Leu
            20                  25                  30

Arg Cys Gln Cys Ile Lys Thr Tyr Ser Lys Pro Phe His Pro Lys Phe
        35                  40                  45

Ile Lys Glu Leu Arg Val Ile Glu Ser Gly Pro His Cys Ala Asn Thr
    50                  55                  60

Glu Ile Ile Val Lys Leu Ser Asp Gly Arg Glu Leu Cys Leu Asp Pro
65                  70                  75                  80

Lys Glu Asn Trp Val Gln Arg Val Val Glu Lys Phe Leu Lys Arg Ala
                85                  90                  95

Glu Asn Ser

<210> SEQ ID NO 2
<211> LENGTH: 1666
<212> TYPE: DNA
<213> ORGANISM: Homo sapiens

<400> SEQUENCE: 2

| | | | | | | |
|---|---|---|---|---|---|---|
| ctccataagg | cacaaacttt | cagagacagc | agagcacaca | agcttctagg | acaagagcca | 60 |
| ggaagaaacc | accggaagga | accatctcac | tgtgtgtaaa | catgacttcc | aagctggccg | 120 |
| tggctctctt | ggcagccttc | ctgatttctg | cagctctgtg | tgaaggtgca | gttttgccaa | 180 |
| ggagtgctaa | agaacttaga | tgtcagtgca | taaagacata | ctccaaacct | ttccacccca | 240 |
| aatttatcaa | agaactgaga | gtgattgaga | gtggaccaca | ctgcgccaac | acagaaatta | 300 |
| ttgtaaagct | ttctgatgga | agagagctct | gtctggaccc | caaggaaaac | tgggtgcaga | 360 |
| gggttgtgga | agagttttttg | aagagggctg | agaattcata | aaaaaattca | ttctctgtgg | 420 |
| tatccaagaa | tcagtgaaga | tgccagtgaa | acttcaagca | atctacttc | aacacttcat | 480 |
| gtattgtgtg | ggtctgttgt | agggttgcca | gatgcaatac | aagattcctg | gttaaatttg | 540 |
| aatttcagta | acaatgaat | agttttttcat | tgtaccatga | aatatccaga | acatacttat | 600 |
| atgtaaagta | ttatttattt | gaatctacaa | aaaacaacaa | ataatttta | aatataagga | 660 |
| ttttcctaga | tattgcacgg | gagaatatac | aaatagcaaa | attgaggcca | agggccaaga | 720 |
| gaatatccga | actttaattt | caggaattga | atgggtttgc | tagaatgtga | tatttgaagc | 780 |
| atcacataaa | aatgatggga | caataaattt | tgccataaag | tcaaatttag | ctggaaatcc | 840 |
| tggatttttt | tctgttaaat | ctggcaaccc | tagtctgcta | gccaggatcc | acaagtcctt | 900 |
| gttccactgt | gccttggttt | ctcctttatt | tctaagtgga | aaaagtatta | gccaccatct | 960 |
| tacctcacag | tgatgttgtg | aggacatgtg | gaagcacttt | aagttttttc | atcataacat | 1020 |
| aaattatttt | caagtgtaac | ttattaacct | atttattatt | tatgtattta | tttaagcatc | 1080 |
| aaatatttgt | gcaagaattt | ggaaaaatag | aagatgaatc | attgattgaa | tagttataaa | 1140 |
| gatgttatag | taaatttatt | ttattttaga | tattaaatga | tgttttatta | gataaatttc | 1200 |
| aatcagggtt | tttagattaa | acaaacaaac | aattgggtac | ccagttaaat | tttcatttca | 1260 |
| gataaacaac | aaataatttt | ttagtataag | tacattattg | tttatctgaa | attttaattg | 1320 |
| aactaacaat | cctagtttga | tactcccagt | cttgtcattg | ccagctgtgt | tggtagtgct | 1380 |
| gtgttgaatt | acggaataat | gagttagaac | tattaaaaca | gccaaaactc | cacagtcaat | 1440 |
| attagtaatt | tcttgctggt | tgaaacttgt | ttattatgta | caaatagatt | cttataatat | 1500 |
| tatttaaatg | actgcatttt | taaatacaag | gctttatatt | tttaacttta | agatgttttt | 1560 |
| atgtgctctc | caatttttt | ttactgtttc | tgattgtatg | gaaatataaa | agtaaatatg | 1620 |
| aaacatttaa | aatataattt | gttgtcaaag | taaaaaaaaa | aaaaaa | | 1666 |

<210> SEQ ID NO 3
<211> LENGTH: 24
<212> TYPE: DNA
<213> ORGANISM: Artificial Sequence
<220> FEATURE:
<223> OTHER INFORMATION: Primer Sequence

<400> SEQUENCE: 3
atgacttcca agctggccgt ggct        24

<210> SEQ ID NO 4

```
<211> LENGTH: 20
<212> TYPE: DNA
<213> ORGANISM: Artificial Sequence
<220> FEATURE:
<223> OTHER INFORMATION: Primer Sequence

<400> SEQUENCE: 4
ttgttgccat caatgacccc                                           20

<210> SEQ ID NO 5
<211> LENGTH: 20
<212> TYPE: DNA
<213> ORGANISM: Artificial Sequence
<220> FEATURE:
<223> OTHER INFORMATION: Primer Sequence

<400> SEQUENCE: 5
tgacaaagtg gtcgttgagg                                           20
```

BIOMARKERS OF TUMOR PHARMACODYNAMIC RESPONSE

RELATED APPLICATIONS

This application claims priority to U.S. Provisional Application No. 61/252,497 filed Oct. 16, 2009, the contents of which is incorporated herein by reference in its entirety.

BACKGROUND OF THE INVENTION

Heat shock protein 90 (Hsp90) is an abundant, ubiquitously expressed member of a multiprotein chaperone complex that mediates the stabilization and maturation of proteins, including several that, when genetically altered, are important for oncogenesis. (Drysdale M J, et al. (2006) Curr. Opin. Drug Discov. Devel. 9(4), 483-495) (Whitesell L, et al. (2005) Nat. Rev. Cancer 5(10), 761-772) To date more than 100 "client" proteins of Hsp90 have been identified, including EGF-R, MET, Raf-1 kinase, AKT, Bcr-abl, mutant p53 and CDK4. (Zhang H, et al. (2004) J. Mol. Med., 82, 488-499) (Xu W, et al. (2001) J. Biol. Chem., 276, 3702-3708)

Hsp90 chaperones, which possess a conserved ATP-binding site at their N-terminal domain (Chene, 2002) belong to a small ATPase sub-family known as the DNA Gyrase, Hsp90, Histidine Kinase and MutL (GHKL) sub-family (Dutta and Inouye, 2000). The chaperoning (folding) activity of Hsp90 depends on its ATPase activity, which is weak for the isolated enzyme. However, it has been shown that the ATPase activity of Hsp90 is enhanced upon its association with proteins known as co-chaperones (Kamal et al., 2003). Therefore, in vivo, Hsp90 proteins work as subunits of large, dynamic protein complexes. Among the stress proteins, Hsp90 is unique because it is not required for the biogenesis of most polypeptides (Nathan et al., 1997). Its cellular targets, also called client proteins, are conformationally labile signal transducers that play a critical role in growth control, cell survival and tissue development (Pratt and Toft, 2003). Inhibition of its intrinsic ATPase activity of Hsp90 disrupts the Hsp90-client protein interaction resulting in their degradation via the ubiquitin proteasome pathway.

The Hsp90 family of chaperones is comprised of four members: Hsp90α and Hsp90β both located in the cytosol, GRP94 in the endoplasmic reticulum, and TRAP1 in the mitochondria (Csermely et al., 1998). Hsp90 is the most abundant cellular chaperone, constituting about 1%-2% of total protein (Jakob and Buchner, 1994). Among the stress proteins, Hsp90 is unique because it is not required for the biogenesis of most polypeptides (Nathan et al., 1997).

Hsp90 is essential for eukaryotic cell survival and is overexpressed in many tumors. In tumor cells, Hsp90 allows oncogenic mutant proteins to maintain or gain function while enabling cancer cells to tolerate the imbalance their presence creates. Hsp90 inhibition hinders these pro-oncogenic effects and leads to significant anti-tumor activity in vivo. (Maloney A, et al. (2003) Curr. Cancer Drug Targets, 3, 331-341) A subset of Hsp90 proteins, such as Raf, AKT, phospho-AKT and CDK4 are oncogenic signaling molecules critically involved in cell growth, differentiation and apoptosis, processes which are important in cancer cells. The degradation of one or multiple oncoproteins is believed to produce the anti-tumor effects observed with Hsp90 inhibitors.

Due to its involvement in regulating a number of signaling pathways that are crucial in driving the phenotype of a tumor, and the discovery that certain bioactive natural products exert their effects via Hsp90 activity, the molecular chaperone Hsp90 is valued as a target for anticancer drug development (Neckers et al., 1999). Many known Hsp90 inhibitors exist for cancer therapy. Among the growing number of therapeutic candidate Hsp90 inhibitors, the benzoquinone ansamycin analogs of geldanamycin, 17-allylamino-17-demethoxygeldanamycin (17-AAG) and 17-dimethylamino-geldanamycin (17-DMAG), are Hsp90 inhibitors that are the furthest advanced in clinial studies. (Solit D B, et al. (2007) Clin. Cancer Res., 13(6), 1775-1782) (Hollingshead M, et al. (2005) Cancer Chemother Pharmacol., 56(2), 115-25) A recently described Hsp90 inhibitor, NVP-AUY922, may hold greater promise via its improved pharmaceutical and pharmacological properties as demonstrated by more potent anti-tumor activity in a preclinical model of human breast cancer. (Jensen M R, et al. (2008) Breast Cancer Res., 10(2), R33) (Eccles S, et al. (2008) Cancer Res, 68(8), 2850-2860) In a panel of representative cancer cell lines, NVP-AUY992 inhibited cell proliferation between 3.6- and 300-fold more effectively than 17-AAG.

Known clinical pharmacodynamic biomarkers of Hsp90 inhibition have proven useful, but many (e.g., measurement of Hsp70 induction) require invasive and laborious procedures such as analyses of nucleated blood cell and/or tumor biopsies. As such, there is a real need to identify convenient, circulating pharmacodynamic markers that can accurately and conveniently reflect the in vivo effect of Hsp90 inhibition in tumors. As described herein, the cytokine IL-8 has been identified as a potential secreted biomarker of tumor cell pharmacodynamic response to HSp90 inhibitors both in vitro and in vivo.

SUMMARY OF THE INVENTION

The present invention provides methods of assessing the efficacy of a treatment regimen for treating cancer in a subject. These methods include contacting a first sample obtained from said subject prior to administering at least a portion of the treatment regimen to the subject with a reagent able to detect IL-8; contacting a second sample obtained from said subject following administration of at least a portion of the treatment regimen with a reagent able to detect IL-8; and comparing the levels of IL-8 from the first and second samples, wherein an elevated level of IL-8 levels present in the first sample, relative to the second sample, is an indication that the treatment regimen is efficacious for treating cancer in the subject. In a particular embodiment, the treatment regimen comprises administration of an Hsp90 inhibitor.

In preferred embodiments, the cancer treatment regimen is for melanoma or gastric cancer.

Detection of IL-8 can occur at the protein level or the level of mRNA expression. Means of detection can include, but are not limited to, antibodies, nucleic acids, and proteins. Detection can also be indirect, such as via observing the interaction between IL-8 and IL-8 receptors (e.g., IL8R1 or IL8R2), or by monitoring Hsp70 levels (as Hsp70 induction results from Hsp90 inhibition).

The present invention also provides methods of identifying a test agent capable of treating cancer, comprising contacting a first sample prior to administering said test agent to the sample with a reagent able to detect IL-8; contacting a second sample obtained from the same source as the first sample following administration of said test agent with a reagent able to detect detect IL-8; and comparing the levels of IL-8 from the first and second samples, wherein an elevated level of IL-8 present in the first sample, relative to the second sample, is an indication that said test agent is capable of treating cancer in the subject.

Said methods can be conducted in vitro or in vivo. The source of the samples can be cancer cell lines, e.g., GTL-16 or A375, can be a transgenic animal exhibiting cancer symptoms, and can be a subject afflicted by cancer.

Other features and advantages of the invention will be apparent from the following detailed description, and from the claims.

DETAILED DESCRIPTION OF THE INVENTION

Figure 1:
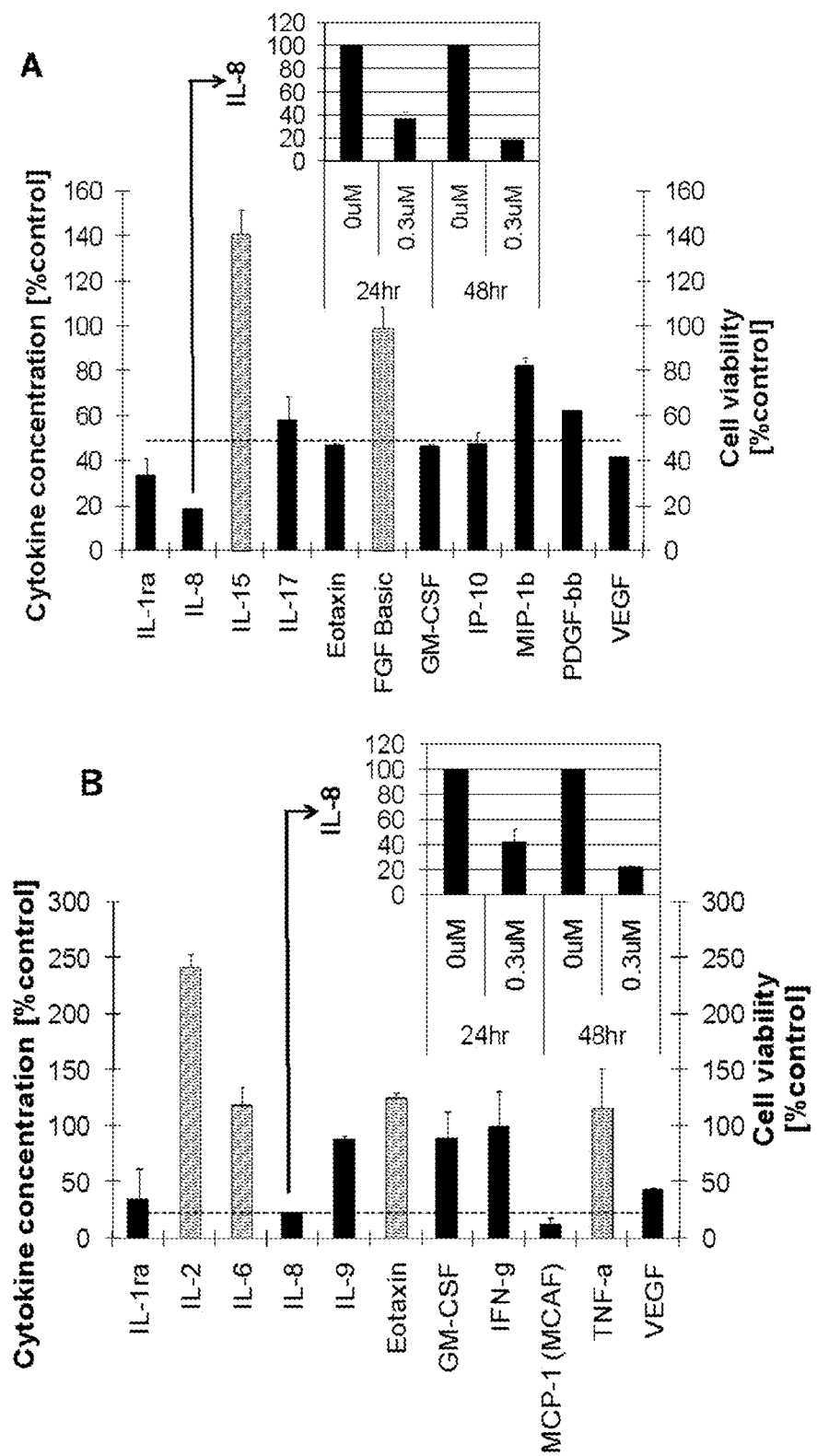
FIG. 1 Relative cytokine levels in cell culture supernatants from (A) GTL-16 and (B) A375 cells that were washed and treated for 48 hr with NVP-AUY922 in fresh culture medium, as measured by multiplex bead-based assay of a 27-plex cytokine panel. Insets show decrease in IL-8 accumulation (as % control) at 24 hr and 48 hr post-treatment with NVP-AUY922. Dotted lines represent cell viability after 48 hr of treatment with NVP-AUY922.

The present invention provides methods of assessing the efficacy of a treatment regimen for treating cancer in a subject. These methods include contacting a first sample obtained from said subject prior to administering at least a portion of the treatment regimen to the subject with a reagent able to detect IL-8; contacting a second sample obtained from said subject following administration of at least a portion of the treatment regimen with a reagent able to detect IL-8; and comparing the levels of IL-8 from the first and second samples, wherein an elevated level of IL-8 levels present in the first sample, relative to the second sample, is an indication that the treatment regimen is efficacious for treating cancer in the subject. In a particular embodiment, the treatment regimen comprises administration of an Hsp90 inhibitor.

In preferred embodiments, the cancer treatment regimen is for melanoma or gastric cancer.

Detection of IL-8 can occur at the protein level or the level of mRNA expression. Means of detection can include, but are not limited to, antibodies, nucleic acids, and proteins. Detection can also be indirect, such as via observing the interaction between IL-8 and IL-8 receptors (e.g., IL8R1 or IL8R2), or by monitoring Hsp70 levels (as Hsp70 induction results from Hsp90 inhibition).

The present invention also provides methods of identifying a test agent capable of treating cancer, comprising contacting a first sample prior to administering said test agent to the sample with a reagent able to detect IL-8; contacting a second sample obtained from the same source as the first sample following administration of said test agent with a reagent able to detect detect IL-8; and comparing the levels of IL-8 from the first and second samples, wherein an elevated level of IL-8 present in the first sample, relative to the second sample, is an indication that said test agent is capable of treating cancer in the subject.

Said methods can be conducted in vitro or in vivo. The source of the samples can be cancer cell lines, e.g., GTL-16 or A375, can be a transgenic animal exhibiting cancer symptoms, and can be a subject afflicted by cancer.

The present invention also provides methods of treating a human subject afflicted with cancer with an Hsp90 inhibitor, the method comprising contacting a first sample from said subject, prior to administering said inhibitor to the subject, with a reagent capable of detecting human IL-8; contacting a second sample obtained from the same source as the first sample, following administration of said inhibitor to said patient, with a reagent capable of detecting human IL-8; measuring the levels of human IL-8 in the first two steps; and comparing the human IL-8 levels obtained in the two steps, wherein an elevated level of human IL-8 in the first step compared to the second step is an indication of therapeutic response by said patient to said inhibitor.

In preferred embodiments, the cancer treatment regimen is for melanoma or gastric cancer.

DEFINITIONS

Various definitions are used throughout this document. Most words have the meaning that would be attributed to those words by one skilled in the art. Words specifically defined either below or elsewhere in this document have the meaning provided in the context of the present invention as a whole and as are typically understood by those skilled in the art.

The practice of the present invention will employ, unless otherwise indicated, conventional methods of chemistry, biochemistry, molecular biology, immunology and pharmacology, within the skill of the art. Such techniques are explained fully in the literature. See, e.g., Remington's Pharmaceutical Sciences, 18th Edition (Easton, Pa.: Mack Publishing Company, 1990); Methods In Enzymology (S. Colowick and N. Kaplan, eds., Academic Press, Inc.); and Handbook of Experimental Immunology, Vols. I-IV (D. M. Weir and C. C. Blackwell, eds., 1986, Blackwell Scientific Publications); and Sambrook et al., Molecular Cloning: A Laboratory Manual (2nd Edition, 1989).

As used herein, the singular forms "a," "an" and "the" include plural references unless the content clearly dictates otherwise. Thus, for example, reference to "an antibody" includes a mixture of two or more such antibodies.

As used herein, the term "about" refers to +/−20%, +/−10%, or +/−5% of a value.

As used herein, the term "IL-8" refers to a potent leukocyte chemotactic and activating cytokine which is produced by numerous types of cells in response to inflammatory stimuli, and whose transcription requires the activation of either the combination of NF-kappa B and AP-1 or that of NF-kappa B and NF-IL6, depending on the type of cells.

An amino acid sequence of IL-8 (GenBank Accession No. NP_000575) is set forth as SEQ ID NO:1, and mRNA sequence of IL-8 (GenBank Accession No. NM_000584) is set forth as SEQ ID NO:2.

A representative IL-8 sequence, includes, but is not limited to, the sequence set forth below.

from a patient who has cancer, or be cells that are transformed in vitro to become cancerous. Cancer cells can be derived from many types of samples including any tissue or cell culture line. In some embodiments the cancer cells are hyperplasias, tumor cells, or neoplasms. In some embodiments, the cancer cells are isolated from colon cancer, liver cancer, testicular cancer, thymus cancer, breast cancer, skin cancer, gastric cancer, esophageal cancer, pancreatic cancer, prostatic cancer, uterine cancer, cervical cancer, lung cancer, bladder cancer, ovarian cancer, multiple myeloma and melanoma. In some embodiments, the cancer cells are taken from established cell lines that are publicly available. In some embodiments, cancer cells are isolated from pre-existing patient samples or from libraries comprising cancer cells. In some embodiments, cancer cells are isolated and then implanted in a different host, e.g., in a xenograft. In some embodiments

```
Interleukin 8 (IL-8) [Homo sapiens] (NP_000575)
                                                           (SEQ ID NO: 1)
   1 MTSKLAVALL AAFLISAALC EGAVLPRSAK ELRCQCIKTY SKPFHPKFIK ELRVIESGPH
  61 CANTEIIVKL SDGRELCLDP KENWVQRVVE KFLKRAENS Interleukin 8 (IL-8) [Homo sapiens] (NM_000584)
                                                           (SEQ ID NO: 2)
   1 ctccataagg cacaaacttt cagagacagc agagcacaca agcttctagg acaagagcca
  61 ggaagaaacc accggaagga accatctcac tgtgtgtaaa catgacttcc aagctggccg
 121 tggctctctt ggcagccttc ctgatttctg cagctctgtg tgaaggtgca gttttgccaa
 181 ggagtgctaa agaacttaga tgtcagtgca taaagacata ctccaaacct ttccacccca
 241 aatttatcaa agaactgaga gtgattgaga gtggaccaca ctgcgccaac acagaaatta
 301 ttgtaaagct ttctgatgga agagagctct gtctggaccc caaggaaaac tgggtgcaga
 361 gggttgtgga gaagttttg aagagggctg agaattcata aaaaaattca ttctctgtgg
 421 tatccaagaa tcagtgaaga tgccagtgaa acttcaagca aatctacttc aacacttcat
 481 gtattgtgtg ggtctgttgt agggttgcca gatgcaatac aagattcctg gttaaatttg
 541 aatttcagta aacaatgaat agtttttcat tgtaccatga aatatccaga acatacttat
 601 atgtaaagta ttatttattt gaatctacaa aaaacaacaa ataattttta aatataagga
 661 ttttcctaga tattgcacgg gagaatatac aaatagcaaa attgaggcca agggcaaga
 721 gaatatccga actttaattt caggaattga atgggtttgc tagaatgtga tatttgaagc
 781 atcacataaa aatgatggga caataaattt tgccataaag tcaaatttag ctggaaatcc
 841 tggattttt tctgttaaat ctggcaaccc tagtctgcta gccaggatcc acaagtcctt
 901 gttccactgt gccttggttt ctcctttatt tctaagtgga aaaagtatta gccaccatct
 961 tacctcacag tgatgttgtg aggacatgtg gaagcacttt aagttttttc atcataacat
1021 aaattatttt caagtgtaac ttattaacct atttattatt tatgtattta tttaagcatc
1081 aaatatttgt gcaagaattt ggaaaaatag aagatgaatc attgattgaa tagttataaa
1141 gatgttatag taaatttatt ttattttaga tattaaatga tgttttatta gataaatttc
1201 aatcagggtt tttagattaa acaaacaaac aattgggtac ccagttaaat tttcatttca
1261 gataaacaac aaataattt ttagtataag tacattattg tttatctgaa attttaattg
1321 aactaacaat cctagtttga tactcccagt cttgtcattg ccagctgtgt tggtagtgct
1381 gtgttgaatt acggaataat gagttagaac tattaaaaca gccaaaactc cacagtcaat
1441 attagtaatt tcttgctggt tgaaacttgt ttattatgta caaatagatt cttataatat
1501 tatttaaatg actgcatttt taaatacaag gctttatatt tttaacttta agatgttttt
1561 atgtgctctc caatttttt ttactgtttc tgattgtatg gaaatataaa agtaaatatg
1621 aaacatttaa aatataattt gttgtcaaag taaaaaaaaa aaaaaa
```

The terms "polypeptide" and "protein", are used interchangeably and refer to a polymeric form of amino acids of any length, which can include coded and non-coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; and the like.

The terms "individual", "subject", "host" and "patient" are used interchangeably and refer to any subject for whom diagnosis, treatment, or therapy is desired, particularly humans. Other subjects may include cattle, dogs, cats, guinea pigs, rabbits, rats, mice, horses, and the like. In some preferred embodiments the subject is a human.

As used herein, "cancer" refers to primary or metastatic cancers, leukemias, or lymphomas. The term "cancer cells" refers to cells that are transformed. These cells can be isolated cancer cells are transplanted and used in a SCID mouse model. In some embodiments, the cancer is colon cancer. As used herein, the term "colon cancer" is used interchangeably with "rectal cancer" and "colorectal cancer," and refers to a cancer that originates in the colon or rectum.

As used herein, the term "transformed" refers to any alteration in the properties of a cell that is stably inherited by its progeny. In some embodiments, "transformed" refers to the change of normal cell to a cancerous cell, e.g., one that is capable of causing tumors. In some embodiments, a transformed cell is immortalized. Transformation can be caused by a number of factors, including overexpression of a receptor in the absence of receptor phosphorylation, viral infection, mutations in oncogenes and/or tumor suppressor genes, and/or any other technique that changes the growth and/or immortalization properties of a cell.

"Cancerous phenotype" generally refers to any of a variety of biological phenomena that are characteristic of a cancerous cell, which phenomena can vary with the type of cancer. The cancerous phenotype is generally identified by abnormalities in, for example, cell growth or proliferation (e.g., uncontrolled growth or proliferation), regulation of the cell cycle, cell mobility, cell-cell interaction, or metastasis, or the like.

As used herein, the term "metastasis" refers to a cancer which has spread to a site distant from the origin of the cancer, e.g. from the primary tumor. Sites of metastasis include without limitation, the bone, lymph nodes, lung, liver, and brain.

As used herein, the term "angiogenesis" refers to the growth of new blood vessels from pre-existing vessels.

As used herein, the term "clinical endpoint" refers to a measurable event indicative of cancer. Clinical endpoints include without limitation, time to first metastasis, time to subsequent metastasis, size and/or number of metastases, size and/or number of tumors, location of tumors, aggressiveness of tumors, quality of life, pain and the like. Those skilled in the art are credited with the ability to determine and measure clinical endpoints. Methods of measuring clinical endpoints are known to those of skill in the art.

As used herein, the term "sample" refers to biological material from a patient. The sample assayed by the present invention is not limited to any particular type. Samples include, as non-limiting examples, single cells, multiple cells, tissues, tumors, biological fluids, biological molecules, or supernatants or extracts of any of the foregoing. Examples include tissue removed for biopsy, tissue removed during resection, blood, urine, lymph tissue, lymph fluid, cerebrospinal fluid, mucous, and stool samples. The sample used will vary based on the assay format, the detection method and the nature of the tumors, tissues, cells or extracts to be assayed. Methods for preparing samples are well known in the art and can be readily adapted in order to obtain a sample that is compatible with the method utilized.

As used herein, the term "biological molecule" includes, but is not limited to, polypeptides, nucleic acids, and saccharides.

As used herein, the term "modulating" refers to a change in the quality or quantity of a gene, protein, or any molecule that is inside, outside, or on the surface of a cell. The change can be an increase or decrease in expression or level of the molecule. The term "modulates" also includes changing the quality or quantity of a biological function/activity including, without limitation, cell proliferation, growth, adhesion, apoptosis, intracellular signaling, cell-to-cell signaling, and the like.

As used herein, the term "differentially expressed in a cancer cell" and "a polynucleotide that is differentially expressed in a cancer cell" are used interchangeably herein, and refer to a polynucleotide that represents or corresponds to a gene that is differentially expressed in a cancerous cell when compared with a cell of the same cell type that is not cancerous, e.g., mRNA is found at levels at least about 25%, at least about 50% to about 75%, at least about 90%, at least about 1.5-fold, at least about 2-fold, at least about 5-fold, at least about 10-fold, or at least about 50-fold or more, different (e.g., higher or lower). The comparison can be made in tissue, for example, if one is using in situ hybridization or another assay method that allows some degree of discrimination among cell types in the tissue. The comparison may also or alternatively be made between cells removed from their tissue source, or between one cell in situ and a second cell removed from its tissue source. In some embodiments, the gene is upregulated in the cancer gene as compared to the normal cell.

The term "fragment" as used herein refers to a physically contiguous portion of the primary structure of a biomolecule. In the case of proteins, a portion is defined by a contiguous portion of the amino acid sequence of that protein and refers to at least 3-5 amino acids, at least 8-10 amino acids, at least 11-15 amino acids, at least 17-24 amino acids, at least 25-30 amino acids, and at least 30-45 amino acids. In the case of oligonucleotides, a portion is defined by a contiguous portion of the nucleic acid sequence of that oligonucleotide and refers to at least 9-15 nucleotides, at least 18-30 nucleotides, at least 33-45 nucleotides, at least 48-72 nucleotides, at least 75-90 nucleotides, and at least 90-130 nucleotides. In some embodiments, portions of biomolecules have a biological activity.

As used herein, the term "antibody" refers to monoclonal and polyclonal antibodies, single chain antibodies, chimeric antibodies, bifunctional/bispecific antibodies, humanized antibodies, human antibodies, and complementary determining region (CDR)-grafted antibodies, that are specific for the target protein or fragments thereof. The term "antibody" further includes in vivo therapeutic antibody gene transfer. Antibody fragments, including Fab, Fab', F(ab')2, scFv, and Fv are also provided by the invention.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations that include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., *Nature* 256:495 (1975), or may be made by recombinant DNA methods (see, e.g., U.S. Pat. No. 4,816,567). The "monoclonal antibodies" may also be isolated from phage antibody libraries using the techniques described in Clackson et al., *Nature* 352:624-628 (1991) and Marks et al., *J. Mol. Biol.* 222:581-597 (1991), for example.

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., Proc. Natl. Acad. Sci. USA, 81:6851-6855 (1984)). Chimeric antibodies of interest herein include "primatized" antibodies comprising variable domain antigen-binding sequences derived from a non-human primate (e.g. Old World Monkey, Ape etc) and human constant region sequences.

"Antibody fragments" comprise a portion of an intact antibody, preferably comprising the antigen-binding or variable region thereof. Examples of antibody fragments include Fab, Fab', F(ab')2, and Fv fragments; diabodies; linear antibodies (Zapata et al., Protein Eng. 8(10): 1057-1062 [1995]); single-chain antibody molecules; and multispecific antibodies formed from antibody fragment(s).

An "intact" antibody is one that comprises an antigen-binding variable region as well as a light chain constant domain ($C_L$) and heavy chain constant domains, $C_{H1}$, $C_{H2}$ and $C_{H3}$. The constant domains may be native sequence constant domains (e.g. human native sequence constant domains) or amino acid sequence variants thereof. In some embodiments, the intact antibody has one or more effector functions.

Antibody "effector functions" refer to those biological activities attributable to the Fc region (a native sequence Fc region or amino acid sequence variant Fc region) of an antibody. Examples of antibody effector functions include C1q binding; complement dependent cytotoxicity; Fc receptor binding; antibody-dependent cell-mediated cytotoxicity (ADCC); phagocytosis; down regulation of cell surface receptors (e.g. B cell receptor; BCR), etc.

"Antibody-dependent cell-mediated cytotoxicity" or "ADCC" refers to a form of cytotoxicity in which secreted Ig bound onto Fc receptors (FcRs) present on certain cytotoxic cells (e.g., Natural Killer (NK) cells, neutrophils, and macrophages) enable these cytotoxic effector cells to bind specifically to an antigen-bearing target cell and subsequently kill the target cell with cytotoxins. The antibodies "arm" the cytotoxic cells and are absolutely required for such killing. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, *Annu. Rev. Immunol.* 9:457-92 (1991). To assess ADCC activity of a molecule of interest, an in vitro ADCC assay, such as that described in U.S. Pat. No. 5,500,362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. (*USA*) 95:652-656 (1998).

"Human effector cells" are leukocytes that express one or more FcRs and perform effector functions. In some embodiments, the cells express at least FcγRIII and perform ADCC effector function. Examples of human leukocytes that mediate ADCC include peripheral blood mononuclear cells (PBMC), natural killer (NK) cells, monocytes, cytotoxic T cells and neutrophils; with PBMCs and NK cells being preferred. The effector cells may be isolated from a native source thereof, e.g. from blood or PBMCs as described herein.

The terms "Fc receptor" or "FcR" are used to describe a receptor that binds to the Fc region of an antibody. The preferred FcR is a native sequence human FcR. Moreover, a preferred FcR is one that binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. (see review M. in Daron, *Annu. Rev. Immunol.* 15:203-234 (1997)). FcRs are reviewed in Ravetch and Kinet, *Annu. Rev. Immunol.* 9:457-92 (1991); Capel et al., *Immunomethods* 4:25-34 (1994); and de Haas et al., *J. Lab. Clin. Med.* 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., *J. Immunol.* 117:587 (1976) and Kim et al., *J. Immunol.* 24:249 (1994)).

As used herein, the term "detecting" means to establish, discover, or ascertain evidence of an activity (for example, gene expression) or biomolecule (for example, a polypeptide).

As used herein, the term "probe" refers to nucleic acid sequences of variable length. In some embodiments probes comprise at least about 10 and as many as about 6,000 nucleotides. In some embodiments probes comprise at least 12, at least 14, at least 16, at least 18, at least 20, at least 25, at least 50 or at least 75 consecutive nucleotides. Probes are used in the detection of identical, similar, or complementary nucleic acid sequences. Longer length probes are usually obtained from natural or recombinant sources, are highly specific to the target sequence, and are much slower to hybridize to the target than are oligomers. Probes may be single- or double-stranded and are designed to have specificity in PCR, hybridization membrane-based, in situ hybridization (ISH), fluorescent in situ hybridization (FISH), or ELISA-like technologies.

As used herein, the term "mixing" refers to the process of combining one or more compounds, cells, molecules, and the like together in the same area. This may be performed, for example, in a test tube, petri dish, or any container that allows the one or more compounds, cells, or molecules, to be mixed.

As used herein the term "isolated" refers to a polynucleotide, a polypeptide, an antibody, or a host cell that is in an environment different from that in which the polynucleotide, the polypeptide, or the antibody naturally occurs. Methods of isolating cells are well known to those skilled in the art. A polynucleotide, a polypeptide, or an antibody which is isolated is generally substantially purified.

As used herein, the term "substantially purified" refers to a compound (e.g., either a polynucleotide or a polypeptide or an antibody) that is removed from its natural environment and is at least 60% free, at least 75% free, and at least 90% free from other components with which it is naturally associated.

As used herein, the term "binding" means the physical or chemical interaction between two or more biomolecules or compounds. Binding includes ionic, non-ionic, hydrogen bonds, Van der Waals, hydrophobic interactions, etc. Binding can be either direct or indirect; indirect being through or due to the effects of another biomolecule or compound. Direct binding refers to interactions that do not take place through or due to the effect of another molecule or compound but instead are without other substantial chemical intermediates.

As used herein, the term "contacting" means bringing together, either directly or indirectly, one molecule into physical proximity to a second molecule. The molecule can be in any number of buffers, salts, solutions, etc. "Contacting" includes, for example, placing a polynucleotide into a beaker, microtiter plate, cell culture flask, or a microarray, or the like, which contains a nucleic acid molecule. Contacting also includes, for example, placing an antibody into a beaker, microtiter plate, cell culture flask, or microarray, or the like, which contains a polypeptide. Contacting may take place in vivo, ex vivo, or in vitro.

As used herein, the phrase "stringent hybridization conditions" or "stringent conditions" refers to conditions under which a probe, primer, or oligonucleotide will hybridize to its target sequence, but to a minimal number of other sequences. Stringent conditions are sequence-dependent and will be different in different circumstances. Longer sequences will hybridize with specificity to their proper complements at higher temperatures. Generally, stringent conditions are selected to be about 5° C. lower than the thermal melting point (Tm) for the specific sequence at a defined ionic strength and pH. The Tm is the temperature (under defined ionic strength, pH and nucleic acid concentration) at which 50% of the probes complementary to the target sequence hybridize to the target sequence at equilibrium. Since the target sequences are generally present in excess, at $T_m$, 50% of the probes are hybridized to their complements at equilibrium. Typically, stringent conditions will be those in which the salt concentration is less than about 1.0 M sodium ion, typically about 0.01 to 1.0 M sodium ion (or other salts) at pH 7.0 to 8.3 and the temperature is at least about 30° C. for short probes, primers or oligonucleotides (e.g., 10 to 50 nucleotides) and at least about 60° C. for longer probes, primers or oligonucleotides. Stringent conditions may also be achieved with the addition of destabilizing agents, such as formamide.

As used herein, the term "moderate stringency conditions" refers to conditions under which a probe, primer, or oligonucleotide will hybridize to its target sequence, but to a limited number of other sequences. Moderate conditions are sequence-dependent and will be different in different circumstances. Moderate conditions are well-known to the art skilled and are described in, inter alfa, Maniatis et al. (Molecular Cloning: A Laboratory Manual, Cold Spring Harbor Laboratory; 2nd Edition (December 1989)).

The nucleic acid compositions described herein can be used, for example, to produce polypeptides, as probes for the detection of mRNA in biological samples (e.g., extracts of human cells) or cDNA produced from such samples, to generate additional copies of the polynucleotides, to generate ribozymes or oligonucleotides (single and double stranded), and as single stranded DNA probes or as triple-strand forming oligonucleotides. The probes described herein can be used to, for example, determine the presence or absence of the polynucleotides provided herein in a sample. The polypeptides can be used to generate antibodies specific for a polypeptide associated with cancer, which antibodies are in turn useful in diagnostic methods, prognostic methods, and the like as discussed in more detail herein. Polypeptides are also useful as targets for therapeutic intervention, as discussed in more detail herein. Antibodies of the present invention may also be used, for example, to purify, detect, and target the polypeptides of the present invention, including both in vitro and in vivo diagnostic and therapeutic methods. For example, the antibodies are useful in immunoassays for qualitatively and quantitatively measuring levels of the polypeptides of the present invention in biological samples. See, e.g., Harlow et al., Antibodies: A Laboratory Manual, (Cold Spring Harbor Laboratory Press, 2nd ed. 1988). These and other uses are described in more detail below.

As used herein the term "imaging agent" refers to a composition linked to an antibody, small molecule, or probe of the invention that can be detected using techniques known to the art-skilled. As used herein, the term "evidence of gene expression" refers to any measurable indicia that a gene is expressed.

The term "pharmaceutically acceptable carrier" refers to a carrier for administration of a therapeutic agent, such as antibodies or a polypeptide, genes, and other therapeutic agents. The term refers to any pharmaceutical carrier that does not itself induce the production of antibodies harmful to the individual receiving the composition, and which can be administered without undue toxicity. Suitable carriers can be large, slowly metabolized macromolecules such as proteins, polysaccharides, polylactic acids, polyglycolic acids, polymeric amino acids, amino acid copolymers, lipid aggregates and inactive virus particles. Such carriers are well known to those of ordinary skill in the art. Pharmaceutically acceptable carriers in therapeutic compositions can include liquids such as water, saline, glycerol and ethanol. Auxiliary substances, such as wetting or emulsifying agents, pH buffering substances, and the like, can also be present in such vehicles.

Heat Shock Proteins (HSPs)

Molecular chaperones maintain the appropriate folding and conformation of proteins and are crucial in regulating the balance between protein synthesis and degradation. They have been shown to be important in regulating many important cellular functions, such as cell proliferation and apoptosis (Jolly and Morimoto, 2000; Smith et al., 1998; Smith, 2001).

Exposure of cells to a number of environmental stresses, including heat shock, alcohols, heavy metals and oxidative stress, results in the cellular accumulation of a number of chaperones, commonly known as heat shock proteins (HSPs). Induction of HSPs protects the cell against the initial stress insult, enhances recovery, and leads to maintenance of a stress tolerant state.

It has also become clear, however, that certain HSPs may also play a major molecular chaperone role under normal, stress-free conditions by regulating the correct folding, degradation, localization and function of a growing list of important cellular proteins.

A number of multigene families of HSPs exist, with individual gene products varying in cellular expression, function and localization. They are classified according to molecular weight, e.g., HSP70, Hsp90, and HSP27.

Several diseases in humans can be acquired as a result of protein misfolding (reviewed in Tytell et al., 2001; Smith et al., 1998). Hence the development of therapies which disrupt the molecular chaperone machinery may prove to be beneficial. In some conditions (e.g., Alzheimer's disease, prion diseases, and Huntington's disease), misfolded proteins can cause protein aggregation resulting in neurodegenerative disorders. Also, misfolded proteins may result in loss of wild type protein function, leading to deregulated molecular and physiological functions in the cell.

HSPs have been implicated in cancer. For example, there is evidence of differential expression of HSPs which may relate to the stage of tumor progression (Martin et al., 2000; Conroy et al., 1996; Kawanishi et al., 1999; Jameel et al., 1992; Hoang et al., 2000; Lebeau et al., 1991). As a result of the involvement of Hsp90 in various critical oncogenic pathways and the discovery that certain natural products with anticancer activity are targeting this molecular chaperone, the concept developed that inhibiting HSP function may be useful in the treatment of cancer. Molecular chaperone inhibitors are currently undergoing clinical trials.

Hsp90 constitutes about 1-2% of total cellular protein, and is usually present in the cell as a dimer in association with one of a number of other proteins (see, e.g., Pratt, 1997). It is essential for cell viability and it exhibits dual chaperone functions (Young et al., 2001). It plays a key role in the cellular stress response by interacting with many proteins after their native conformation has been altered by various environmental stresses, such as heat shock, ensuring adequate protein folding and preventing non-specific aggregation (Smith et al., 1998). In addition, results suggest that Hsp90 may also play a role in buffering against the effects of mutation, presumably by correcting the inappropriate folding of mutant proteins (Rutherford and Lindquist, 1998).

However, Hsp90 also has an important regulatory role. Under normal physiological conditions, together with its endoplasmic reticulum homologue GRP94, Hsp90 plays a housekeeping role in the cell, maintaining the conformational stability and maturation of several key client proteins. These can be subdivided into three groups: (a) steroid hormone receptors, (b) Ser/Thr or tyrosine kineses (e.g., ERBB2, RAF-1, CDK4, and LCK), and (c) a collection of apparently unrelated proteins, e.g., mutant p53 and the catalytic subunit of telomerase hTERT. All of these proteins play key regulatory roles in many physiological and biochemical processes in the cell. New Hsp90 client proteins are continuously being identified.

The highly conserved Hsp90 family in humans consists of four genes, namely the cytosolic Hsp90α and Hsp90β isoforms (Hickey et al., 1989), GRP94 in the endoplasmic reticulum (Argon et al., 1999), and HSP75/TRAP1 in the mitochondrial matrix (Felts et al., 2000). It is thought that all the family members have a similar mode of action, but bind to different client proteins depending on their localization within the cell. For example, ERBB2 is known to be a specific client protein of GRP94 (Argon et al., 1999) and type 1 tumour necrosis factor receptor (TNFR1) and RB have both been shown to be clients of TRAP1 (Song et al., 1995; Chen et al., 1996).

Hsp90 participates in a series of complex interactions with a range of client and regulatory proteins (Smith, 2001). Although the precise molecular details remain to be elucidated, biochemical and X-ray crystallographic studies (Prodromou et al., 1997; Stebbins et al., 1997) carried out over the last few years have provided increasingly detailed insights into the chaperone function of Hsp90.

Hsp90 is an ATP-dependent molecular chaperone (Prodromou et al, 1997), with dimerization of the nucleotide binding domains being essential for ATP hydrolysis, which is in turn essential for chaperone function (Prodromou et al, 2000a). Binding of ATP results in the formation of a toroidal dimer structure in which the N terminal domains are brought into closer contact with each other resulting in a conformational switch known as the "clamp mechanism" (Prodromou and Pearl, 2000b).

Hsp90 Inhibitors

Inhibition of Hsp90 function has been shown to cause selective degradation of important signalling proteins involved in cell proliferation, cell cycle regulation and apoptosis, processes which are fundamentally important and which are commonly deregulated in cancer (see, e.g., Hostein et al., 2001).

Inhibition of Hsp90 ATPase activity prevents recruitment of co-chaperones and encourages the formation of a type of Hsp90 heterocomplex from which these client proteins are targeted for degradation via the ubiquitin proteasome pathway (see, e.g., Neckers et al., 1999; Kelland et al., 1999). Treatment with Hsp90 inhibitors leads to selective degradation of important proteins involved in cell proliferation, cell cycle regulation and apoptosis, processes which are fundamentally important in cancer.

An attractive rationale for developing drugs against this target for use in the clinic is that by simultaneously depleting proteins associated with the transformed phenotype, one may obtain a strong antitumour effect and achieve a therapeutic advantage against cancer versus normal cells. These events downstream of Hsp90 inhibition are believed to be responsible for the antitumour activity of Hsp90 inhibitors in cell culture and animal models (see, e.g., Schulte et al., 1998; Kelland et al., 1999).

Due to its involvement in regulating a number of signaling pathways that are crucially important in driving the phenotype of a tumor, and the discovery that certain bioactive natural products exert their effects via Hsp90 activity, the molecular chaperone Hsp90 is valued as a target for anticancer drug development (Neckers et al., 1999). Many known Hsp90 inhibitors exist for cancer therapy.

The first class of Hsp90 inhibitors to be discovered was the benzoquinone ansamycin class, which includes the compounds herbimycin A and geldanamycin. They were shown to reverse the malignant phenotype of fibroblasts transformed by the v-Src oncogene (Uehara et al., 1985), and subsequently to exhibit potent antitumour activity in both in vitro (Schulte et al., 1998) and in vivo animal models (Supko et al., 1995).

Immunoprecipitation and affinity matrix studies have shown that the major mechanism of action of geldanamycin involves binding to Hsp90 (Whitesell et al., 1994; Schulte and Neckers, 1998). Moreover, X-ray crystallographic studies have shown that geldanamycin competes at the ATP binding site and inhibits the intrinsic ATPase activity of Hsp90 (Prodromou et al., 1997; Panaretou et al., 1998). This in turn prevents the formation of mature multimeric Hsp90 complexes capable of chaperoning client proteins. As a result, the client proteins are targeted for degradation via the ubiquitin proteasome pathway. 17-Allylamino, 17-demethoxygeldanamycin (17MG) retains the property of Hsp90 inhibition resulting in client protein depletion and antitumour activity in cell culture and xenograft models (Schulte et al, 1998; Kelland et al, 1999), but has significantly less hepatotoxicity than geldanamycin (Page et al, 1997). 17MG is currently being evaluated in Phase I clinical trials.

Coumarin antibiotics are known to bind to bacterial DNA gyrase at an ATP binding site homologous to that of the Hsp90. The coumarin, novobiocin, was shown to bind to the carboxy terminus of Hsp90, i.e., at a different site to that occupied by the benzoquinone ansamycins and radicicol which bind at the N-terminus (Marcu et at, 2000b). However, this still resulted in inhibition of Hsp90 function and degradation of a number of Hsp90-chaperoned signalling proteins (Marcu et al., 2000a). Geldanamcyin cannot bind Hsp90 subsequent to novobiocin; this suggests that some interaction between the N and C terminal domains must exist and is consistent with the view that both sites are important for Hsp90 chaperone properties.

A purine-based Hsp90 inhibitor, PUS, has been shown to result in the degradation of signalling molecules, including ERBB2, and to cause cell cycle arrest and differentiation in breast cancer cells (Chiosis et al., 2001).

Treatment of cancer cells with an mTOR inhibitor can cause up-regulation of the pro-survival protein phospho-AKT (O'Reilly, 2006). Since phospho-AKT is an Hsp90 client protein, co-treatment of a mTOR inhibitor with an Hsp90 inhibitor would prevent or diminish the mTOR inhibitor induced upregulation of phospho-AKT giving rise to an increased anti-tumor effect.

Currently, three Hsp90 inhibitors in clinical, several others in pre-clinical development. 17-AAG, co-developed by Kosan and NCI, is a geldanamycin analogue and was the first into clinic. 17-AAG now in Ph II trials as single agent in melanoma, breast cancer, RCC, ovarian cancer, and prostate cancer. Several Ph Ib combinations studies with gemcitabine, docetaxel, paclitaxel, rituxamib, imatinib, and bortezomib in solid and hematological tumors ongoing. 17-DMAG the second geldanamycin developed by Kosan now in Ph I trials in solid tumors and hematological tumors. CNF 1010, developed by Conforma, is an organic solvent-free formulation of 17-AAG and is currently in Ph I in solid tumor and CML.

Other Hsp90 inhibitors in pre-clinical developments include IPI-504 (Infinity Pharma), CGI 242 (Cellular Genomics), SRN 005 (Sirenade), Stresgenin (Mercian Group), and unnamed compounds from Memorial Sloan-Kettering Cancer Center and Quorex.

As described herein, many secreted proteins were investigated to assess their ability to serve as circulating indicators of tumor response to pharmacologic inhibition of Hsp90. The cytokine IL-8 in particular was found to function well as a secreted biomarker of tumor cell pharmacodynamic response to NVP-AUY922 both in vitro and in vivo. Further investigation of a mechanistic link provided evidence consistent with the hypothesis that IL-8 expression is affected by Hsp90 inhibitors through their effects on proteins that regulate the transcriptional activity of the IL-8 gene, namely AP-1 and NFκB. IL-8 is a promising pharmacodynamic biomarker of Hsp90 inhibition in the context of tumors known to express high levels of this chemokine.

Among the growing number of therapeutic candidate Hsp90 inhibitors, the benzoquinone ansamycin analogs of geldanamycin, 17-allylamino-17-demethoxygeldanamycin (17-AAG) and 17-dimethylamino-geldanamycin (17-DMAG), are Hsp90 inhibitors that are the furthest advanced in clinial studies. (Solit D B, et al. (2007) Clin. Cancer Res., 13(6), 1775-1782) (Hollingshead M, et al. (2005) Cancer Chemother Pharmacol., 56(2), 115-25) A recently described Hsp90 inhibitor, NVP-AUY922, may hold greater promise via its improved pharmaceutical and pharmacological properties as demonstrated by more potent anti-tumor activity in a preclinical model of human breast cancer. (Jensen M R, et al. (2008) Breast Cancer Res., 10(2), R33) (Eccles S, et al. (2008) Cancer Res, 68(8), 2850-2860) In a panel of representative cancer cell lines, NVP-AUY992 inhibited cell proliferation between 3.6- and 300-fold more effectively than 17-AAG. A description of AUY922 and other related Hsp90 inhibitors can also be found in patent publication WO04/72051.

Biomarkers of Hsp Inhibition

The recent emergence of Hsp90 inhibitors as potential anticancer agents comes with the need for relevant biomarkers indicating in vivo pharmacodynamic effect in tumors. There are several well-established biomarkers of Hsp90 inhibition, such as increased Hsp70 expression and decreased levels of several cancer-relevant signaling molecules but their measurement typically requires laborious and invasive comparative analysis of pre- and post-treatment biopsies. (Banerji U, et al. (2005) 23(18), 4152-4161) This has led to investigation of tumor-derived secreted or shed proteins whose levels are potentially changed in response to Hsp90 inhibition. Recently a breast cancer study evaluated IGFBP-2 and the shed extracellular domain of Her2 (Her2-ECD), both of which may have promise as circulating pharmacodynamic markers for a subset of tumors overexpressing these proteins. (Zhang H, et al. (2006) Mol. Cancer. Ther., 5(5), 1256-1264)

Since the stabilities of multiple client proteins are affected by Hsp90 chaperone complex activity, the relative abundance of each client in certain tumors can serve as a pharmacodynamic indicator of Hsp90 inhibitor activity, such as AKT (Sato S, et al. (2000) PNAS, 97(20), 10832-10837), ErbB2 (Xu, 2001), and Cdk4 (Stepanova L, et al. (1996) Genes Develop., 10, 1491-1502) In addition to destabilization of client proteins, pharmacologic inhibition of Hsp90 also leads to increased expression of the stress response protein, Hsp70. This is accomplished via activation of HSF-1 through its dissociation from Hsp90 and subsequent translocation to the nucleus, where it activates transcription of multiple genes, including Hsp70. (Shi Y, et al. (1998) Genes and Devel., 12(5), 654-666)

The utilization of specific client protein degradation and/or Hsp70 induction as clinical pharmacodynamic biomarkers of Hsp90 inhibition has proven to be useful, but requires invasive and laborious procedures such as analyses of nucleated blood cell and/or tumor biopsies. Circulating pharmacodynamic markers are therefore preferred, and can accurately and conveniently reflect the in vivo effect of Hsp90 inhibition in tumors. Two such proteins, insulin-like growth factor 2 (IGFBP-2) and shed Her-2 extracellular domain (ECD), were identified in vitro and in serum from a BT474 breast tumor xenograft model (Zhang H, et al. (2006) Mol. Cancer. Ther., 5(5), 1256-1264), and their evaluation as clinical biomarkers has only been tested in a small number of patient samples. (Eiseman J L, et al. (2007) Clin. Cancer Res., 13(7), 2121-2127) While a more comprehensive study in patients will be required to understand the utility of IGFBP-2 and Her-2 ECD as potential pharmacodynamic biomarkers of Hsp90 inhibition, it is likely that tumor heterogeneity will lead to the need for multiple tumor-derived secreted or shed proteins.

As described herein, the potential utility of IL-8 as a circulating biomarker of tumor pharmacodynamic response to Hsp90 inhibition significantly contributes to the cancer biomarker field. The recently described Hsp90 inhibitor, NVP-AUY922, blocked the production of IL-8 in a dose dependent manner in gastric and melanoma cell lines that are known to express relatively high levels of this cytokine. This decrease in IL-8 production appears to occur with more rapid kinetics than the loss of cell viability and can be attributed to disruption of IL-8 mRNA expression in these cells. The observed loss of phospho-c-Jun (a subunit of AP-1) and, to a lesser extent, NFκB levels suggest a mechanistic link to pharmacologic inhibition of Hsp90, consistent with reports that the activity of both transcription factors are dependent on activity of the Hsp90 chaperone complex. (Pittet J F, et al. (2005) J. Immun., 174(1), 384-394)(Broemer M, et al. (2004) Oncogene, 5378-5386)(Vasileskaya I A, et al. (1999) Cancer Res., 59, 3935-3940) (Lu C, et al. (2007) Mol. Cells, 24(2), 210-214)(Duo F, et al. (2005) Acta Biochim. Biophys. Sinica, 37(7), 501-505) Furthermore, a single dose of NVP-AUY922 resulted in a transient 40-70% decrease in serum IL-8 levels in tumor-bearing mice, indicating that IL-8 expressing tumor responses to Hsp90 inhibitors can be assessed by measuring this cytokine in circulation.

Elevated IL-8 expression levels have been reported in multiple cancer cell lines, including breast (Chavey C, et al. (2008) Mol. Pharmacol., 74(5), 1359-1366), cervical (Fujimoto J, et al. (2006) Cancer Sci., 97(9), 861-867), melanoma (Peng H H, et al. (2007) Exp. Cell Res., 313(3), 551-559), gastric (Kim J M, et al. (2003) Helicobacter, 8(5), 542-553)(Kitadai Y, et al. (1999) Br. J. Cancer. 81(4), 647-653), ovarian (Wang Y, et al. (2007) Cancer Biol. Ther., 6(6), 864-871), and prostate (Golovine K, et al. (2008) Prostate, 68(13), 1443-9). Serum or plasma IL-8 levels have been measured in multiple cancer patient studies, including gastric (MacRi A, et al. (2006) Biomarkers, 11(2), 184-193) (Yamaoka Y, et al. (2001) Helicobacter, 6(20), 116-124), melanoma (Yurkovetsky Z R, et al. (2007) Clin. Cancer Res., 13(8), 2422-2428)(Guida M, et al. (2006) Melan. Res., 16(4), 317-323), and lung (Tas F, et al. (2006) Cancer Invest., 24(5), 492-496) cancer and are generally observed to be 10- to 100-fold higher than in patients with most of the potentially confounding conditions. In addition, IL-8 levels in healthy individuals are very low, within the confines of the assay utilized for measurement. The rapid inhibition of tumor-derived IL-8 production in response to Hsp90 inhibition points to its potential utility for a subset of cancers that express high levels of IL-8. Therefore, IL-8 could be a very informative circulating biomarker of tumor pharmacodynamic response to Hsp90 inhibition for the subset of tumors that express high levels of this cytokine.

It is not likely that a single circulating biomarker will be universally relevant for Hsp90 inhibitors or other anticancer agents across all cancer types, or even for tumors within a currently defined cancer type. Therefore there is a need to discover multiple potential biomarkers to informatively monitor pharmacodynamic responses to maximize the fraction of "monitorable" tumors in the patient population. The results described validated IL-8 as another useful pharmacodynamic marker in gastric and melanoma cancer. In addition to Her-2 ECD, IGFBP-2, and now IL-8, the cytokine multiplex analysis also suggests there are a number of other potential markers that may have similar utility, such as IL-1ra, IL-17, VEGF and GM-CSF that may serve as markers for yet another subset of tumors. In conclusion, this study shows that NVP-AUY922, a potent inhibitor of Hsp90, rapidly blocks production of IL-8 in gastric and melanoma tumor cells in vitro and in vivo. Furthermore, published data indicate there might be a significant differential between tumor-derived IL-8 as opposed to non-tumor-derived IL-8 levels in circulation, facilitating the non-invasive detection of tumor-specific pharmacodynamic effect. These results warrant further characterization of IL-8 as a circulating pharmacodynamic biomarker of tumor Hsp90 inhibition, including assessment of its utility in clinical studies.

IL-8

Cells utilize diffusible mediators, called cytokines, to signal one another. A superfamily of cytokines are the chemokines, which includes 1IL-8. A review article of the chemokine superfamily was written by Miller et al., Crit Rev Immun 12(1,2): 17-46 (1992) and by Baggiolini et al. Adv Immunol 55: 97-179 (1994), herein incorporated by reference.

Native human IL-8 acts as a chemoattractant for neutrophils, and induces granulocytosis upon systemic injection and skin reaction upon local injection in experimental animals. (Bazzoni et al., (1991) 173: 771-774; Van Damme et al., J En Med 167: 1364-1376; Ribero et al., Immunology 73: 472-477 (1991)). The molecule also activates the release of superoxide anions and elicits release of primary granule constituents of neutrophils, including myeloperoxidase, β-glucuronidase, and elastase. Native human IL-8 mediates these biological activities by binding to its receptor and triggering transduction, a cascade of reactions ultimately resulting in a biological response.

Presently, two IL-8 binding receptors have been identified and are termed "IL-8R1" and "EUR2." The amino acid sequence of these polypeptides are described in Murphy et al., Science 253: 1280 (1991) and Holmes et al., Science 253: 1278 (1991), herein incorporated by reference. Other proteins can compete with IL-8 to bind to IL-8R2, such as GROα, GROβ, and GROγ. NAP-2 AND ENA-78 have been implicated with IL-8R.2 binding by cross-desensitization experiments with native IL-8 by measuring $Ca^{2+}$.

These other proteins which can compete for IL-8 binding are members of the chemokine family. The chemokines are a group of structurally and functionally related cytokines. Recent studies indicated that these proteins function in the recruitment and activation of leukocytes and other cells at sites of inflammation and, therefore, appear to be important inflammatory mediators. Structurally, these molecules exhibit common secondary protein structure and display four conserved cysteine residues. The common secondary structures of a chemokine include: (1) an amino terminal loop; (2) a three stranded antiparallel 13 sheet in the form of a Greek key; and (3) an C-terminal cc helix. Because a systematic nomenclature for these proteins has not yet been generally agreed upon, the proteins can be divided into two families according to the spacing of the first two cysteine residues of the mature proteins. The families are referred to as the CXC and CC family. The first two cysteine residues of the CXC family members are separated by an amino acid residue. For the CC family, the cysteines are not separated. To date, seventeen chemokines have been described. Six are members of the CXC family and include, platelet factor 4 ("PF4"); β-thromboglobulin ("βTG"); NAP-I/IL-8; groα, β, and γ; IP-10; mig; and ENA-78. The CXC family is also known as the α family. The remaining chemokines are part of the CC family: macrophage inflammatory proteins ("MIP-1α" and "MIP-1β"); monocyte chemoattractant protein-1/JE ("MCP-1"/"JE") RANTES; HC-14; C10; and I-309. This family has also been designated as the β family.

Researchers have identified regions of native human IL-8 that are implicated in both IL-8R1 and IL-8R2 binding. However, at this time, no chemokine is known to compete with native IL-8 for IL-8R1 binding.

Assays

The presence, absence, and/or level of IL-8 in a biological sample obtained from a subject may be assessed by any of a wide variety of in vitro and in vivo techniques and methods, which transform IL-8 within the sample into a moiety that can be detected and quantified. Non-limiting examples of such methods include analyzing the sample using immunological methods for detection of proteins, protein purification methods, protein function or activity assays, nucleic acid hybridization methods, nucleic acid reverse transcription methods, and nucleic acid amplification methods, enzyme linked immunosorbent assays (ELISAs), immunoblotting, Western blotting, Northern blotting, electron microscopy, mass spectrometry, immunoprecipitation, immunofluorescence, Southern hybridizations and the like. Such techniques, as well as others described herein, can also be used to detect additional markers of Hsp90 inhibition and/or of cancer treatment regimens, including, but not limited to IL-1ra, IL-17, Eotaxin, GM-CSF, IP-10, PDGF-bb, phospho-ERK1/2, phospho-c-Jun, Hsp70, AKT, ErbB2, Cdk4, IGFBP-2, Her-2 extracellular domain (ECD), and VEGF, IL-15, where applicable.

In one embodiment, the presence, absence, and/or level of IL-8 in a sample can be assessed using a reagent, such as an antibody (e.g., a radio-labeled, chromophore-labeled, fluorophore-labeled, or enzyme-labeled antibody), an antibody derivative (e.g., an antibody conjugated with a substrate or with the protein or ligand of a protein-ligand pair (e.g. biotin-streptavidin)), or an antibody fragment (e.g., a single-chain antibody or an isolated antibody hypervariable domain) which binds specifically to and transforms the biomarker, e.g., IL-8, in a sample into a detectable molecule.

The term "labeled", with regard to the antibody, is intended to encompass direct labeling of the antibody by coupling (i.e., physically linking) a detectable substance to the antibody, as well as indirect labeling of the antibody by reactivity with another reagent that is directly labeled. Examples of indirect labeling include detection of a primary antibody using a fluorescently labeled secondary antibody, such that it can be detected with fluorescently labeled streptavidin.

In another embodiment, the presence, absence, and/or level of IL-8 is assessed using a nucleic acid. For example, in one embodiment, the presence, absence, and/or level of IL-8 is assessed using a nucleic acid probe.

The term "probe," as used herein, refers to any molecule that is capable of selectively binding to IL-8. Probes can be synthesized by one of skill in the art, or derived from appropriate biological preparations. Probes may be specifically designed to be labeled. Examples of molecules that can be utilized as probes include, but are not limited to, RNA, DNA, proteins, antibodies, and organic molecules.

Isolated mRNA can be used in hybridization or amplification assays that include, but are not limited to, Southern or Northern analyses, polymerase chain reaction analyses and probe arrays. One method for the detection of mRNA levels involves contacting the isolated mRNA with a nucleic acid molecule (probe) that can hybridize to IL-8 mRNA. The nucleic acid probe can be, for example, a full-length cDNA, or a portion thereof, such as an oligonucleotide of at least 7, 15, 30, 50, 100, 250 or 500 nucleotides in length and sufficient to specifically hybridize under stringent conditions to IL-8 genomic DNA.

In one embodiment, the mRNA is immobilized on a solid surface and contacted with a probe, for example by running the isolated mRNA on an agarose gel and transferring the mRNA from the gel to a membrane, such as nitrocellulose. In an alternative embodiment, the probe(s) are immobilized on a solid surface and the mRNA is contacted with the probe(s), for example, in an Affymetrix gene chip array. A skilled artisan can readily adapt known mRNA detection methods for use in detecting the level of IL-8 mRNA.

An alternative method for determining the level of IL-8 mRNA in a sample involves the process of nucleic acid amplification, e.g., by RT-PCR (the experimental embodiment set forth in Mullis, 1987, U.S. Pat. No. 4,683,202), ligase chain reaction (Barany (1991) *Proc. Natl. Acad. Sci. USA* 88:189-193), self sustained sequence replication (Guatelli et al. (1990) *Proc. Natl. Acad. Sci. USA* 87:1874-1878), transcriptional amplification system (Kwoh et al. (1989) *Proc. Acad. Acad. Sci. USA* 86:1173-1177), Q-Beta Replicase (Lizardi et al. (1988) *Bio/Technology* 6:1197), rolling circle replication (Lizardi et al., U.S. Pat. No. 5,854,033) or any other nucleic acid amplification method, followed by the detection of the amplified molecules using techniques well known to those of skill in the art. These detection schemes are especially useful for the detection of nucleic acid molecules if such molecules are present in very low numbers. In particular aspects of the invention, IL-8expression is assessed by quantitative fluorogenic RT-PCR (i.e., the TaqMan™ System). Such methods typically utilize pairs of oligonucleotide primers that are specific for IL-8. Methods for designing oligonucleotide primers specific for a known sequence are well known in the art.

The expression levels of IL-8 mRNA may be monitored using a membrane blot (such as used in hybridization analysis such as Northern, Southern, dot, and the like), or microwells, sample tubes, gels, beads or fibers (or any solid support comprising bound nucleic acids). See U.S. Pat. Nos. 5,770,722, 5,874,219, 5,744,305, 5,677,195 and 5,445,934, which are incorporated herein by reference. The detection of IL-8 expression may also comprise using nucleic acid probes in solution.

In one embodiment of the invention, microarrays are used to detect IL-8 expression. Microarrays are particularly well suited for this purpose because of the reproducibility between different experiments. DNA microarrays provide one method for the simultaneous measurement of the expression levels of large numbers of genes. Each array consists of a reproducible pattern of capture probes attached to a solid support. Labeled RNA or DNA is hybridized to complementary probes on the array and then detected by laser scanning. Hybridization intensities for each probe on the array are determined and converted to a quantitative value representing relative gene expression levels. See, U.S. Pat. Nos. 6,040,138, 5,800,992 and 6,020,135, 6,033,860, and 6,344,316, which are incorporated herein by reference. High-density oligonucleotide arrays are particularly useful for determining the gene expression profile for a large number of RNA's in a sample.

Furthermore, in vivo techniques for detection of IL-8 include introducing into a subject a labeled antibody directed against IL-8, which binds to and transforms IL-8 into a detectable molecule. As discussed above, the presence, level, or even location of the detectable IL-8 in a subject may be detected determined by standard imaging techniques.

In another embodiment, mass spectrometry can be used to detect IL-8 in a sample. Mass spectrometry is an analytical technique that consists of ionizing chemical compounds to generate charged molecules (or fragments thereof) and measuring their mass-to-charge ratios. In a typical mass spectrometry procedure, a sample is obtained from a subject, loaded onto the mass spectrometry, and its components (e.g., IL-8) are ionized by different methods (e.g., by impacting them with an electron beam), resulting in the formation of charged particles (ions). The mass-to-charge ratio of the particles is then calculated from the motion of the ions as they transit through electromagnetic fields.

For diagnostic applications, the antibody typically will be labeled with a detectable moiety. Numerous labels are available which can be generally grouped into the following categories:

(a) Radionuclides such as those discussed infra. The antibody can be labeled, for example, with the radioisotope using the techniques described in Current Protocols in Immunology, Volumes 1 and 2, Coligen et al., Ed. Wiley-Interscience, New York, N.Y., Pubs. (1991) for example and radioactivity can be measured using scintillation counting.

(b) Fluorescent labels such as rare earth chelates (europium chelates) or fluorescein and its derivatives, rhodamine and its derivatives, dansyl, Lissamine, phycoerythrin and Texas Red are available. The fluorescent labels can be conjugated to the antibody using the techniques disclosed in Current Protocols in Immunology, supra, for example. Fluorescence can be quantified using a fluorimeter.

(c) Various enzyme-substrate labels are available and U.S. Pat. No. 4,275,149 provides a review of some of these. The enzyme generally catalyzes a chemical alteration of the chromogenic substrate which can be measured using various techniques. For example, the enzyme may catalyze a color change in a substrate, which can be measured spectrophotometrically. Alternatively, the enzyme may alter the fluorescence or chemiluminescence of the substrate. Techniques for quantifying a change in fluorescence are described above. The chemiluminescent substrate becomes electronically excited by a chemical reaction and may then emit light which can be measured (using a chemiluminometer, for example) or donates energy to a fluorescent acceptor. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRPO), alkaline phosphatase, beta-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Techniques for conjugating enzymes to antibodies are described in O'Sullivan et al., Methods for the Preparation of Enzyme-Antibody Conjugates for use in Enzyme Immunoassay, in Methods in Enzym. (ed J. Langone & H. Van Vunakis), Academic press, New York, 73:147-166 (1981).

The antibodies may also be used for in vivo diagnostic assays. In some embodiments, the antibody is labeled with a radionuclide so that the tumor can be localized using immunoscintiography. As a matter of convenience, the antibodies of the present invention can be provided in a kit, i.e., a packaged combination of reagents in predetermined amounts with instructions for performing the diagnostic assay. Where the antibody is labeled with an enzyme, the kit may include substrates and cofactors required by the enzyme (e.g., a substrate precursor which provides the detectable chromophore or fluorophore). In addition, other additives may be included such as stabilizers, buffers (e.g., a block buffer or lysis buffer) and the like. The relative amounts of the various reagents may be varied widely to provide for concentrations in solution of the reagents which substantially optimize the sensitivity of the assay. Particularly, the reagents may be provided as dry powders, usually lyophilized, including excipients which on dissolution will provide a reagent solution having the appropriate concentration.

In some embodiments, antibodies are conjugated to one or more maytansine molecules (e.g. about 1 to about 10 maytansine molecules per antibody molecule). Maytansine may, for example, be converted to May-SS-Me which may be reduced to May-SH3 and reacted with modified antibody (Chari et al. Cancer Research 52: 127-131 (1992)) to generate a maytansinoid-antibody immunoconjugate. In some embodiments, the conjugate may be the highly potent maytansine derivative DM1 (N2'-deacetyl-N2'-(3-mercapto-1-oxopropyl)-maytansine) (see for example WO02/098883 published Dec. 12, 2002) which has an IC50 of approximately 10-11 M (review, see Payne (2003) Cancer Cell 3:207-212) or DM4 (N2'-deacetyl-N2'(4-methyl-4-mercapto-1-oxopentyl)-maytansine) (see for example WO2004/103272 published Dec. 2, 2004).

In some embodiments the antibody conjugate comprises an anti-tumor cell antigen antibody conjugated to one or more calicheamicin molecules. The calicheamicin family of antibiotics is capable of producing double-stranded DNA breaks at sub-picomolar concentrations. Structural analogues of calicheamicin which may be used include, but are not limited to, gamma1I, alpha2I, alpha3I, N-acetyl-gamma1I, PSAG and theta1I (Hinman et al. Cancer Research 53: 3336-3342 (1993) and Lode et al. Cancer Research 58: 2925-2928 (1998)). See, also, U.S. Pat. Nos. 5,714,586; 5,712,374; 5,264,586; and 5,773,001, each of which is expressly incorporated herein by reference.

In some embodiments the antibody is conjugated to a prodrug capable of being released in its active form by enzymes overproduced in many cancers. For example, antibody conjugates can be made with a prodrug form of doxorubicin wherein the active component is released from the conjugate by plasmin. Plasmin is known to be over produced in many cancerous tissues (see Decy et al, (2004) FASEB Journal 18(3): 565-567).

In some embodiments the antibodies are conjugated to enzymatically active toxins and fragments thereof. In some embodiments the toxins include, without limitation, diphtheria A chain, nonbinding active fragments of diphtheria toxin, exotoxin A chain (from *Pseudomonas aeruginosa*), Pseudomonas endotoxin, ricin A chain, abrin A chain, modeccin A chain, alpha-sarcin, Aleurites fordii proteins, dianthin proteins, *Phytolaca americana* proteins (PAPI, PAPII, and PAP-S), Ribonuclease (Rnase), Deoxyribonuclease (Dnase), pokeweed antiviral protein, momordica charantia inhibitor, curcin, crotin, sapaonaria officinalis inhibitor, gelonin, mitogellin, restrictocin, phenomycin, neomycin and the tricothecenes. See, for example, WO 93/21232 published Oct. 28, 1993. In some embodiments the toxins have low intrinsic immunogenicity and a mechanism of action (e.g. a cytotoxic mechanism versus a cytostatic mechanism) that reduces the opportunity for the cancerous cells to become resistant to the toxin.

In some embodiments conjugates are made between the antibodies of the invention and immunomodulators. For example, in some embodiments immunostimulatory oligonucleotides can be used. These molecules are potent immunogens that can elicit antigen-specific antibody responses (see Datta et al, (2003) Ann N.Y. Acad. Sci. 1002: 105-111). Additional immunomodulatory compounds can include stem cell growth factor such as "S1 factor", lymphotoxins such as tumor necrosis factor (TNF), hematopoietic factor such as an interleukin, colony stimulating factor (CSF) such as granulocyte-colony stimulating factor (G-CSF) or granulocyte macrophage-stimulating factor (GM-CSF), interferon (IFN) such as interferon alpha, beta or gamma, erythropoietin, and thrombopoietin.

In some embodiments radioconjugated antibodies are provided. In some embodiments such antibodies can be made using $^{32}P$, $^{33}P$, $^{47}Sc$, $^{59}Fe$, $^{64}Cu$, $^{67}Cu$, $^{75}Se$, $^{77}As$, $^{89}Sr$, $^{90}Y$, $^{99}Mo$, $^{105}Rh$, $^{109}Pd$, $^{125}I$, $^{131}I$, $^{142}Pr$, $^{143}Pr$, $^{149}Pm$, $^{153}Sm$, $^{161}Th$, $^{166}Ho$, $^{169}Er$, $^{177}Lu$, $^{186}Re$, $^{188}Re$, $^{189}Re$, $^{194}Ir$, $^{198}Au$, $^{199}Au$, $^{211}Pb$, $^{212}Pb$, $^{213}Bi$, $^{58}Co$, $^{67}Ga$, $^{80m}Br$, $^{99m}Tc$, $^{103m}Rh$, $^{109}Pt$, $^{161}Ho$, $^{189m}Os$, $^{192}Ir$, $^{152}Dy$, $^{211}At$, $^{212}Bi$, $^{223}Ra$, $^{219}Rn$, $^{215}Po$, $^{211}Bi$, $^{225}Ac$, $^{221}Fr$, $^{217}At$, $^{213}Bi$, $^{255}Fm$ and combinations and subcombinations thereof. In some embodiments, boron, gadolinium or uranium atoms are conjugated to the antibodies. In some embodiments the boron atom is $^{10}B$, the gadolinium atom is $^{157}Gd$ and the uranium atom is $^{235}U$.

In some embodiments the radionuclide conjugate has a radionuclide with an energy between 20 and 10,000 keV. The radionuclide can be an Auger emitter, with an energy of less than 1000 keV, a P emitter with an energy between 20 and 5000 keV, or an alpha or 'a' emitter with an energy between 2000 and 10,000 keV.

In some embodiments diagnostic radioconjugates are provided which comprise a radionuclide that is a gamma-, beta-, or positron-emitting isotope. In some embodiments the radionuclide has an energy between 20 and 10,000 keV. In some embodiments the radionuclide is selected from the group of $^{18}F$, $^{51}Mn$, $^{52}Fe$, $^{62}Cu$, $^{64}Cu$, $^{68}Ga$, $^{72}As$, $^{75}Br$, $^{76}Br$, $^{82m}Rb$, $^{83}Sr$, $^{89}Zr$, $^{94m}Tc$, $^{51}Cr$, $^{57}Co$, $^{58}Co$, $^{59}Fe$, $^{67}Ga$, $^{75}Se$, $^{97}Ru$, $^{99m}Tc$, $^{114m}In$, $^{123}I$, $^{125}I$, $^{13}Li$ and $^{197}Hg$.

In some embodiments the antibodies of the invention are conjugated to diagnostic agents that are photoactive or contrast agents. Photoactive compounds can comprise compounds such as chromagens or dyes. Contrast agents may be, for example a paramagnetic ion, wherein the ion comprises a metal selected from the group of chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and erbium (III). The contrast agent may also be a radio-opaque compound used in X-ray techniques or computed tomography, such as an iodine, iridium, barium, gallium and thallium compound. Radio-opaque compounds may be selected from the group of barium, diatrizoate, ethiodized oil, gallium citrate, iocarmic acid, iocetamic acid, iodamide, iodipamide, iodoxamic acid, iogulamide, iohexyl, iopamidol, iopanoic acid, ioprocemic acid, iosefamic acid, ioseric acid, iosulamide meglumine, iosemetic acid, iotasul, iotetric acid, iothalamic acid, iotroxic acid, ioxaglic acid, ioxotrizoic acid, ipodate, meglumine, metrizamide, metrizoate, propyliodone, and thallous chloride. In some embodiments, the diagnostic immunoconjugates may contain ultrasound-enhancing agents such as a gas filled liposome that is conjugated to an antibody of the invention. Diagnostic immunoconjugates may be used for a variety of procedures including, but not limited to, intraoperative, endoscopic or intravascular methods of tumor or cancer diagnosis and detection.

In some embodiments antibody conjugates are made using a variety of bifunctional protein coupling agents such as N-succinimidyl-3-(2-pyridyldithiol) propionate (SPDP), succinimidyl-4-(N-maleimidomethyl)cyclohexane-1-carboxylate, iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al. Science 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of the cytotoxic drug in the cell. For example, an acid-labile linker, peptidase-sensitive linker, dimethyl linker or disulfide-containing linker (Chari et al. Cancer Research 52: 127-131 (1992)) may be used. Agents may be additionally linked to the antibodies of the invention through a carbohydrate moiety.

In some embodiments fusion proteins comprising the antibodies of the invention and cytotoxic agents may be made, e.g. by recombinant techniques or peptide synthesis. In some embodiments such immunoconjugates comprising the antitumor antigen antibody conjugated with a cytotoxic agent are administered to the patient. In some embodiments the immunoconjugate and/or tumor cell antigen protein to which it is bound is/are internalized by the cell, resulting in increased therapeutic efficacy of the immunoconjugate in killing the cancer cell to which it binds. In some embodiments, the cytotoxic agent targets or interferes with nucleic acid in the cancer cell. Examples of such cytotoxic agents include maytansinoids, calicheamicins, ribonucleases and DNA endonucleases.

In some embodiments the antibodies are conjugated to a "receptor" (such as streptavidin) for utilization in tumor pre-targeting wherein the antibody-receptor conjugate is administered to the patient, followed by removal of unbound conjugate from the circulation using a clearing agent and then administration of a "ligand" (e.g. avidin) which is conjugated to a cytotoxic agent (e.g. a radionucleotide).

In some embodiments the antibodies are conjugated to a cytotoxic molecule which is released inside a target cell lysozome. For example, the drug monomethyl auristatin E (MMAE) can be conjugated via a valine-citrulline linkage which will be cleaved by the proteolytic lysozomal enzyme cathepsin B following internalization of the antibody conjugate (see for example WO03/026577 published Apr. 3, 2003). In some embodiments, the MMAE can be attached to the antibody using an acid-labile linker containing a hydrazone functionality as the cleavable moiety (see for example WO02/088172 published Nov. 11, 2002).

Kits

The invention also provides kits for assessing whether a subject has or is at risk for developing cancer. These kits comprise devices and reagents for measuring gene expression and/or determining mRNA and/or peptide levels in a subject's sample and instructions for performing the assay and interpreting the results. Such kits preferably contain sufficient reagents to perform one or more such determinations. These kits include one or more of the following: a detectable moiety, e.g., an antibody or PCR probe, that is able to detect IL-8, phospho-ERK1/2, or phospho-c-Jun; reagents for obtaining and/or preparing samples for staining; and instructions for use.

In another aspect, the present invention provides a kit for the analysis of gene expression and/or peptide levels. Such a kit preferably comprises devices and reagents for the analysis of at least one test sample and instructions for performing the assay. Optionally the kits may contain one or more means for converting gene expression and/or amounts of peptides to a means of assessing the efficacy of a treatment regimen for treating cancer in a subject. Comparison of the subject's gene expression pattern, with the controls or reference standards, would indicate whether the cancer treatment regimen is working properly.

The kits of the invention may optionally comprise additional components useful for performing the methods of the invention. By way of example, the kits may comprise fluids (e.g., SSC buffer) suitable for annealing complementary nucleic acids or for binding an antibody with a protein with which it specifically binds, one or more sample compartments, an instructional material which describes performance of a method of the invention and tissue specific controls/standards.

The present invention is further illustrated by the following examples which should not be construed as further limiting.

EXAMPLES

Identification of IL-8 As a Circulating Biomarker for Hsp90 Inhibition

Materials and Methods

Cell Culture

A malignant melanoma cell line A375 (American Type Culture Collection, Manassas, Va., USA) and gastric cancer cell line, GTL-16 (Prof Silvia Giordano, Institute for Cancer Research and Treatment, Turin, Italy) were cultured in RPMI 1640 supplemented with 10% FBS and 1% penicillin-streptomycin at 37° C. in 5% $CO_2$ (GIBCO reagents, Invitrogen Corporation, Carlsbad, Calif., USA). Cell numbers were determined by ViCell™ XR Cell Viability Analyzer 2.03 (Beckman Coulter, Inc., Fullerton, Calif., USA). Cells were seeded in poly-D-lysine coated plates (BIOCOAT Cell Environments, Becton Dickinson Biosciences, San Jose, Calif., USA).

Hsp90 Inhibitor Compound, NVP-AUY922

NVP-AUY922 (IUPAC name: 5-(2,4-Dihydroxy-5-isopropyl-phenyl)-4-(4-morhpolin-4-ylmethyl-phenyl)-isoxazole-3-carboxylic acid ethylamide) is based on an isoxazole-3-caroxylic acid scaffold. The identification and structure of NVP-AUY922 have been described previously. (Jensen, 2008) (Brough, P A, et al. (2008) J Med Chem, 51, 196-218) (patent publication WO04/72051) For all in vitro experiments, 10 mM stock solutions of NVP-AUY922 were prepared in 100% dimethyl sulfoxide (DMSO) and stored at −20° C. For in vivo experiments, a salt of NVP-AUY922 was dissolved in D5W and delivered i.v. in a volume of 10 mL/kg.

The structure of NVP-AUY922 is as follows:

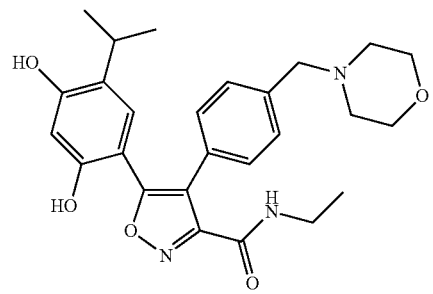 [SMILES: CCNC(=O)c1noc(-c2cc(C(C)C)c(O)cc2O)c1-c1ccc(CN2CCOCC2)cc1]

Cell Viability

Cell Viability was measured by CellTiter-Glo assay (Promega U.S., Madison, Wis., USA). GTL-16 and A375 cells were grown in 6-well poly-D-lysine coated plates (BD Biosciences). Cells were treated with NVP-AUY922. Cell viability was measured 16, 24, 48 and 72 hr post-treatment with Hsp90 inhibitor. Briefly supernatants were removed and cells were washed with 3 ml of PBS, pH 7.4. 1 ml of a two component CellTiter-Glo reagent was added to each well and the plates were shaken vigorously for 2 min, followed by 10 min incubation at room temperature in the dark. Luminescent signal intensity was recorded with an integration time set between 0.25 and 1 s/well.

GTL-16 and A375 Mouse Xenograft Models

The in vivo study was carried out in strict accordance with Swiss law for animal protection and was approved by the Swiss Cantonal Veterinary Office of Basel-Stadt. GTL-16 ($4 \times 10^6$) and A375 cells ($5 \times 10^6$) were inoculated subcutaneously in the right flank in 200 µl Hanks' balanced salt solution (HBSS) or PBS, respectively. Invasive procedures were performed under Forene anesthesia. All experiments were performed in female Harlan HsdNpa: Athymic Nude-nu mice (Laboratory Animal Services, Novartis Pharma AG, Basel). The animals were kept under optimized hygienic conditions with 12 hr dark, 12 hr light conditions. The animals were fed food and water ad libitum. A single 75 mg/kg and 50 mg/kg dose of Hsp90 inhibitor, NVP-AUY922 was administered to the GTL-16 and A375 tumor-bearing mice, when tumors had reached a mean volume of 200 $mm^3$-500 $mm^3$ in size. Mice in the control group were injected with the vehicle (D5W). Serum was isolated and tumors dissected over the time course 0-168 hr. Tumors were cut in two halves. One half was paraffin embedded and the other snap frozen, and stored at –80° C.

Enzyme-Linked ImmunoSorbent Assay

Human IL-8 levels in cell culture supernatants from GTL-16 and A375 cells were measured by a sandwich enzyme-linked immunosorbent assay (R&D Systems, Inc., Minneapolis, Minn., USA). Cell culture supernatants were collected from DMSO and NVP-AUY922 treated cells 16, 24, 48 and 72 hr post-treatment and stored at –20° C.

BioPlex Bead-Based Assay

Human IL-8 levels in cell culture supernatants treated with NVP-AUY922 were initially assessed as part of a multiplexed bead-based cytokine panel (hu 27-plex panel I, Bio-rad Laboratories, Hercules, Calif., USA) with a BioPlex Suspension Array System (Bio-rad). Human IL-8 and mouse KC levels in serum derived from GTL-16 and A375 tumor-bearing mice treated with NVP-AUY922 were measured by single-plex cytokine bead-based assay (Milliplex, Millipore, Billerica, Mass., USA). The BioPlex system uses a liquid suspension array of beads. The beads align in a single file through a flow cell to the detector, where a red classification laser at a wavelength of 635 nm and a green reporter laser at a wavelength of 532 nm are used to identify each bead's spectral address and associated reporter signal, respectively.

Quantitative Reverse Transcription-PCR

Total cellular RNA was extracted from the GTL-16 and A375 cell lines using RNeasy mini kit (Qiagen, Inc., Valencia, Calif., USA). Total RNA quantitation was carried out using a RiboGreen assay (Invitrogen Corporation, Carlsbad, Calif., USA). 1 µg of total RNA was reverse transcribed using AMV reverse transcriptase (Reverse Transcription Kit, Promega U.S., Madison, Wis., USA). A 20 µl reaction cocktail was prepared as follows; 1 µg total RNA in 10 µl of RNase, DNase-free $H_2O$, 4 µl of 25 mM $MgCl_2$, 2 µl of 10× reverse transcriptase buffer, 2 µl of 10 mM dNTP's, 1 µl of 500 µg $ml^{-1}$ random hexamers, 1.5 µl of 10 µl $ml^{-1}$, and 40 U $µl^{-1}$ 0.5 µl of recombinant RNase Inhibitor. Real time PCR was performed using a 7900HT fast real-time PCR system (Applied Biosystems, Foster City, Calif., USA) using the Power SYBR Green PCR master mix (Applied Biosystems). The primers for IL-8 and GAPDH were: IL-8 sense: 5'-ATGACTTCCAAGCTGGCCGTGGCT-3' (SEQ ID NO:3) and IL-8 antisense:

5'-TCTCAGCCCTCTTCAAAAACTTCT-3' (SEQ ID NO:4); and GAPDH sense:

5'-TTGTTGCCATCAATGACCCC-3' (SEQ ID NO:5), and GAPDH antisense;

5'-TGACAAAGTGGTCGTTGAGG-3'. (SEQ ID NO:6) The amplification process involved an initial 5 min denaturing step at 95° C. This was followed by annealing reactions for both IL-8 and GAPDH, of 45 s at 95° C. with 230 s at 68° C. for 34 cycles and 1 min at 95° C. with 1 min at 60° C. and 1 min 72° C. for 30 cycles, respectively. The final extension was 10 min at 72° C. The comparative $C_T$ method was use to analyze the data.

Protein Extraction

Total protein lysates were prepared from the GTL-16 and A375 cells with RIPA lysis buffer (Upstate, Millipore Corporation, Charlottesville, Va., USA). Cells were washed with PBS and 500 ul of ice-cold RIPA buffer, containing protease inhibitor cocktail tablet (Roche Diagnostic GmbH, Mannheim, Germany) and phosphatase inhibitors (Sigma-Aldrich, Inc., St. Louis, Mo., USA), was added to each plate on ice. After 15 min the cells were scrapped from the plate surface and spun at 16000 RPM for 10 min at 4° C. The supernatant was collected and frozen at –80° C. Nuclear protein fractions were prepared by the NE-PER nuclear and cytoplasmic extraction kit (Pierce Biotechnology, Rockford, Ill., USA). Proteins were quantified by bicinchoninic acid assay (Pierce Biotechnology, Rockford, Ill., USA) for Western blotting.

Western Blot Analysis

Primary antibodies specific for NFκB p65, cREL, p-ERK1/2, p-c-jun, ERK1 and Jun were purchased from Santa Cruz Biotechnology (Santa Cruz Biotechnology, Inc., Santa Cruz, Calif., USA) with the exception of Hsp70 and TBP (nuclear loading control), which were obtained from StressGen (StressGen, Assay Designs, Inc., Aim Arbor, Mich., USA) and Abcam (Abcam Inc., Cambridge, Mass., USA), respectively. 4-12% Bis-Tris SDS-PAGE, denaturing, non-reducing gels were loaded with 30 µg of total protein, a SeeBlue2Plus pre-stained protein standard and MES SDS running buffer were utilized for the electrophoretic separation in a XCell SureLock™ Mini-Cell (Invitrogen Corporation, Inc., Carlsbad, Calif., USA). An iBlot™ gel transfer PVDF stack with iBlot™ gel transfer system (Invitrogen) was used. An Odyssey Infrared Imaging System was used to detect the immunocomplex (Li-COR Biotechnologies, Inc., Lincoln, Nebr., USA). Li-COR blocking buffer was used to limit cross-reactivity. Membranes were incubated at 4° C. overnight in the primary antibody diluted in blocking buffer, followed by 1 hr room temperature incubation with a secondary IgG antibody (Li-COR IR dye, Li-COR).

Immunohistochemistry

Formalin-fixed paraffin embedded tissue sections were stained using the Ventana Discovery System (Ventana Medical Systems, Tucson, Ariz., USA). Deparaffinization of tissue sections and heat-induced epitope retrieval using Standard Cell Conditioning solution 1 (Ventana Medical Systems) were performed directly on the System. A mouse anti-human Hsp70 (Stressgen Bioreagents, MI, USA) was prepared in DAKO diluent (DAKO, Carpinteria, Calif.) and used at the concentration of 10 ug/ml for 60 min. Slides were incubated with a biotin-labeled anti-mouse IgG1 (Research Diagnostic Inc, MA, USA, now known as Fitzgerald Industries International, Concord, Mass., USA) at a concentration of 1.25 ug/ml diluted in M.O.M. (Vector Laboratories, Burlingame, Calif., USA). Detection using a 3,3'-diaminobenzadine reaction was performed on the section, using the Ventana DAB Map reagent for the Hsp70 antibody (Ventana Medical Systems). Each tissue section was subsequently counterstained with haematoxylin to ensure antibody specificity. Consecutive tissue sections were incubated with normal isotype-matched immunoglobulins (mouse IgG1, Lab Vision Corporation, Fremont, Calif., USA) used at equivalent concentration to the Hsp70 antibody. Hsp70 induction in stained tissue sections was quantified utilizing the Aperio ScanScope XT digital slide scanning system (Aperio Technologies, Inc., Vista, Calif., USA) with the Spectrum software (version 9.0.748.1518).

Results

Multiplex Screening of Cytokines in Tumor Cell Culture Supernatants

In a screen for candidate secreted markers of Hsp90 inhibition, cell culture supernatants were collected from GTL-16 gastric carcinoma and A375 melanoma cells that were washed and treated for 48 hr with 1 µM NVP-AUY922 in fresh culture medium. These samples were analyzed by a multiplexed cytokine bead-based assay that included a panel of 27 human cytokines, the results of which are shown in FIG. 1. In GTL-16 cell cultures, inhibitor treatment resulted in decreased accumulation of IL-1ra, IL-8, IL-17, Eotaxin, GM-CSF, IP-10, PDGF-bb and VEGF, increased accumulation of IL-15, while accumulation of FGF basic and MIP-1b remain virtually unchanged. In A375 cell cultures, decreased accumulation of IL-1ra, IL-8, MCP-1 (MCAF) and VEGF, and increased IL-2 levels were observed, whereas accumulation of other detectable cytokines remained unchanged with treatment. Most notably from this multiplexed assay, IL-8 accumulation decreased by more than 80% and 70% in GTL-16 and A375 cell cultures, respectively, which prompted further investigation of IL-8 as a potential biomarker of NVP-AUY922 mediated inhibition of Hsp90. In addition to this empirical investigation using the bead-based immunoassay panel, in silica data mining was undertaken to identify secreted proteins that were regulated by previously reported Hsp90 client proteins; this investigation pointed to a number of candidates, including IL-8, consistent with the empirical results.

In Vitro Dose- and Time-Dependent Inhibition of IL-8 Accumulation in Response to NVP-AUY922

Figure 2:
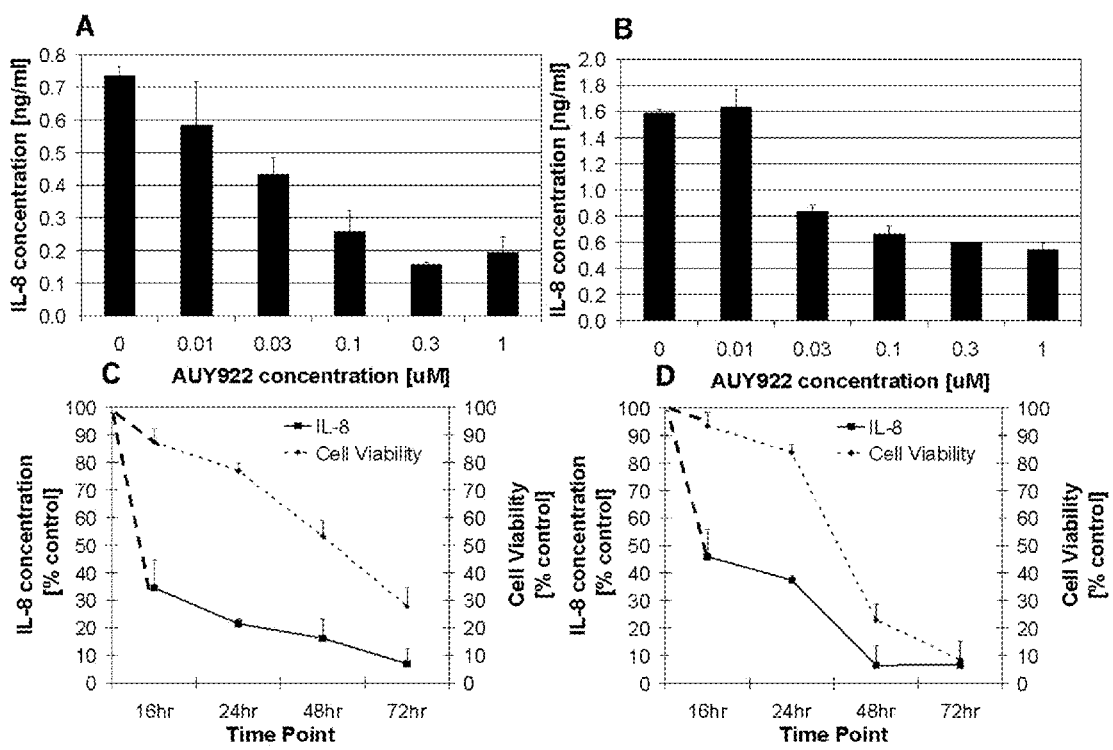
FIG. 2 Dose- and time-dependent effects of NVP-AUY922 on cell viability and on production of IL-8. Upper panel: Cell culture supernatants collected from GTL-16 (A) and A375 (B) cells washed with fresh culture medium and treated with NVP-AUY922 for 24 hr. Lower panel: Cell viability and IL-8 accumulation over the indicated times after treatment of GTL-16 (C) and A375 (D) cells with 0.3 µM NVP-AUY922.

To better characterize the relationship between Hsp90 inhibitor treatment and effects on IL-8 production, GTL-16 and A375 cells were washed and treated for 24 hr with fresh medium containing various concentrations of NVP-AUY922. For this length of treatment time, maximal inhibition of IL-8 accumulation appears to be reached at 0.3 µM as measured by enzyme-linked immunosorbent assay; this equates to 80% and 60% reductions in GTL-16 and A375 cultures, respectively (FIGS. 2A, B). The inhibition of IL-8 production appears to precede the overt loss in cell viability under these conditions, dramatically declining within 16 hr of treatment (FIGS. 2C, D), whereas cell viability steadily declines over the 72 hr treatment time. Similar results were observed in both cell lines treated with a 0.3 µM concentration of 17AAG, suggesting a mechanistic link between Hsp90 inhibition and loss of IL-8 production.

Figure 3:
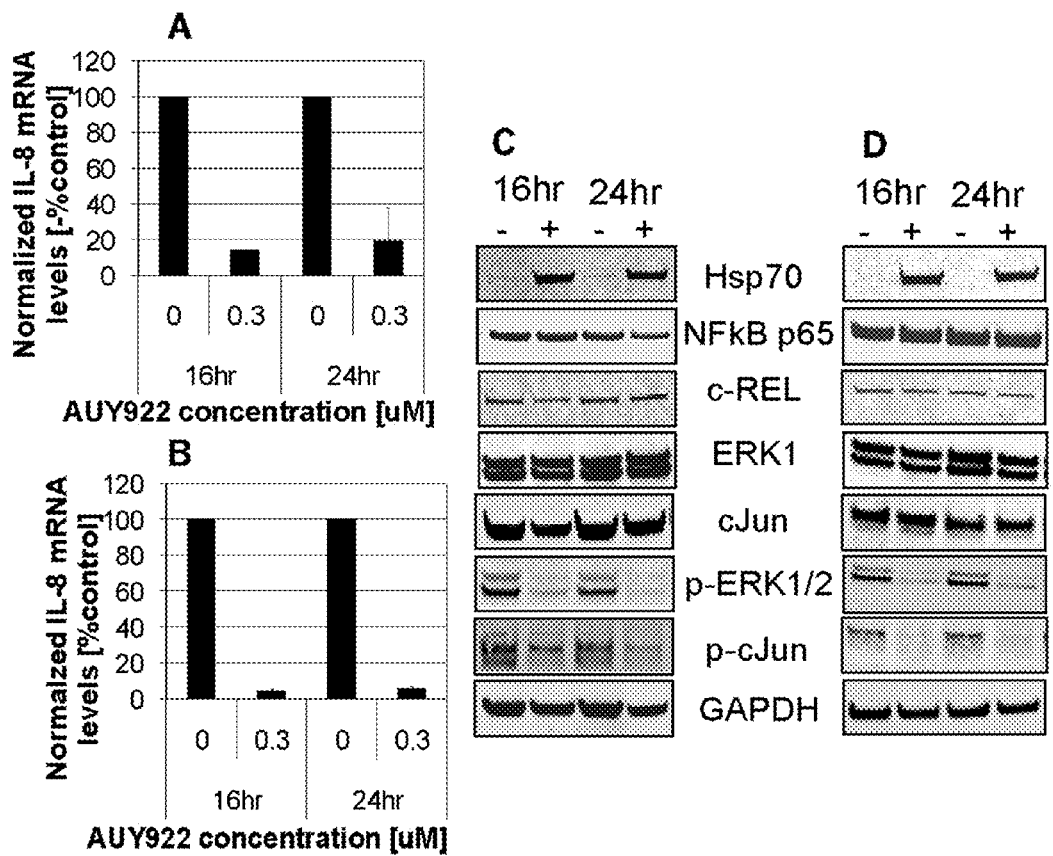
FIG. 3 Effects of NVP-AUY922 on expression of IL-8 mRNA and known regulators of IL-8 gene expression. Quantitative RT-PCR analysis of IL-8 mRNA levels in GTL-16 (A) and A375 (B) cells after treatment with 0.3 µM NVP-AUY922 for the indicated times. Western blot analyses of 30 µg total protein lysates prepared from untreated (−) and 0.3 µM NVP-AUY922 treated (+) GTL-16 (C) and A375 (D) cells.

Effect of NVP-AUY922 on IL-8 mRNA Expression and Known Regulators of IL-8 Gene Transcription Since substantial evidence indicates that the major sites of IL-8 expression are at the level of mRNA expression, mRNA expression was measured after NVP-AUY922 treatment in GTL-16 and A375 cells. (Mukaida N, et al. (1994) J. Leukocyte Biol., 56, 554-558) (Mukaida N, et al. (1990) J. Biol. Chem., 265, 21128-21133) For both cell lines, a dramatic decline in IL-8 mRNA levels is observed after treatment with 0.3 µM NVP-AUY922. At 16 hr, IL-8 mRNA levels are 95% lower in treated versus untreated A375 cells (FIG. 3A), consistent with the changes seen in IL-8 protein accumulation in culture supernatants. A similar response is observed in GTL-16 cells at 16 hr, where an 85% decrease in IL-8 mRNA expression is noted (FIG. 3B). These results suggest that altered IL-8 mRNA expression underlies the response to NVP-AUY922.

IL-8 gene expression is activated by transcription factors NFκB and AP-1. (Roebuck K A (1999) J Interfer. Cyto. Res., 19, 429-438) NFκB is considered essential, whereas AP-1 in conjunction with NFκB enhances IL-8 expression. p65 and c-REL are the two major NFκB family members that activate IL-8 transcription. (Kunsch C, et al. (1993) Mol. Cell Biol., 6137-6146) In order to understand whether NVP-AUY922 affects the activity of AP-1 or NFκB by treatment with NVP-AUY922, total protein extracts were prepared for both GTL-16 and A375 at 16 hr and 24 hr post-treatment with 0.3 µM NVP-AUY922 and signaling proteins associated with these two transcription factors were assessed by Western blot analysis. As a control for the activity of the compound, Hsp70 induction was observed in both the GTL-16 and A375 cell lines treated with 0.3 µM NVP-AUY922 (FIGS. 3C and D), consistent with effective inhibition of Hsp90. From FIGS. 3C and D, it is evident that total cellular levels of the two major NFκB family members, p65 and c-REL, are essentially unchanged after treatment with 0.3 µM NVP-AUY922.

MAP kinase proteins that are primarily involved in regulating AP-1 activity include ERK, p38, and Jun N-terminal protein kinases. (Hoffman E, et al. (2002) J. Leukocyte. Biol., 72, 847-855) (Karin M (1995) J Biol Chem, 270(28), 16483-16486)(Silvers A L, et al. (2003) Neoplasia, 5(4), 319-329) JNK is the most prominent and well understood MAPK signaling pathway that regulates AP-1 activity; in addition, ERK activation leads to elevated AP-1 activity via c-fos induction. (Chen R H, et al. (1993) Proc. Natl. Acad. Sci. USA, 90, 10952-10956) The effects of NVP-AUY922 on MAPK signaling pathway mediators were evaluated by Western blot analysis. Total ERK and c-Jun levels appear to be unaffected after 16 hr and 24 hr of treatment with 0.3 µM NVP-AUY922. However levels of phospho-ERK1/2 and phospho-c-Jun are significantly diminished in both GTL-16 and A375 cells post-treatment. These results are consistent with the possibility that inhibition of the ERK and JNK MAPK pathways results in dramatic loss of AP-1 activity, which would lead to loss of IL-8 gene transcription.

Figure 4:
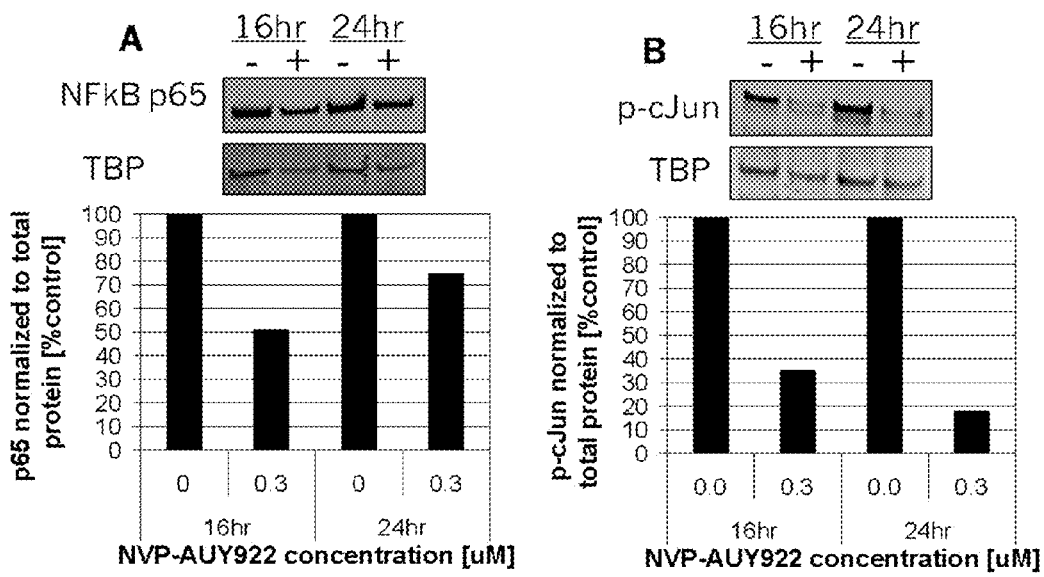
FIG. 4 Nuclear NFkB p65 (A) and phospho-cJun (B) levels at 16 hr and 24 hr post-treatment with NVP-AUY922 in the GTL-6 cell line by Western blot analysis. Semi-quantitative data was calculated by Licor software whereby the signal intensity is measured in K Counts. K count values for NFkB p65 and phospho-c-Jun were normalized to total protein concentrations as measured by BCA assay and plotted as % control.

Although treatment with NVP-AUY922 had no apparent effect on the total cellular levels of key NFκB family members thought to regulate IL-8 gene transcription, it is possible that changes in nuclear NFκB levels may be affected by Hsp90 inhibition. In order to evaluate this possibility, nuclear protein fractions were prepared for GTL-16 cells treated with 0.3 µM NVP-AUY922 for 16 hr and 24 hr; and Western blot analysis was performed for NFκB p65 as well for phospho-c-Jun. A modest decline in nuclear NFκB p65 levels was observed in cells after treatment with NVP-AUY922 (FIG. 4A), although this decrease is eliminated when NFκB levels are normalized to the nuclear protein loading control, TATA binding protein (TBP). It is possible that TBP levels may also be affected by Hsp90 inhibition; total protein levels were utilized as a surrogate control for normalization of NFκB p65 and phospho-c-Jun levels as tabulated in FIG. 4C. Using this normalization, a modest decrease (−26%) was observed in nuclear NFκB p65 levels, whereas a more dramatic decrease in nuclear phospho-c-Jun levels (~83%) is apparent (FIGS. 4A, B). These results are consistent with the hypothesis that loss of AP-1 activity is the predominant mechanism for NVP-AUY922 mediated loss of IL-8 gene transcription in both the A375 and GTL-16 cell lines.

In Vivo Evaluation of Circulating, Tumor-Derived IL-8 as a Pharmacodynamic Biomarker of Hsp90 Inhibition To establish that our findings in vitro translate to an in vivo setting, GTL-16 and A375 tumor-bearing mice were treated with single 75 and 50 mg/kg doses of NVP-AUY922, respectively and IL-8 levels in serum from both models were measured over 168 hr. To confirm NVP-AUY922 activity, Hsp70 expression was measured, in total protein lysates isolated from snap frozen tumor tissue samples, by Western blot (FIG. 5A) and immunohistochemistry (FIG. 5B), since Hsp70 induction is a downstream effect of Hsp90 inhibition. Both measurements show Hsp70 is induced as early as 6 hr post-treatment with NVP-AUY922 with stable Hsp70 induction to 48 hr, at which point the levels subside to a base line level over the time course; this is consistent with previously published data. (Jensen, 2008) The same pattern of Hsp70 induction was established in A375 tumor-bearing mice treated with NVP-AUY922. Since Hsp70 induction is considered a gold standard in establishing that the Hsp90 chaperone complex has been inhibited, we were convinced that NVP-AUY922 was having an inhibitory effect on the GTL-16 and A375 tumors directly, and that if IL-8 was indeed a pharmacodynamic biomarker of Hsp90 inhibition, as the in vitro findings suggest, that would be reflected in the in vivo IL-8 measurement in serum derived from these tumor-bearing mice.

Figure 5:
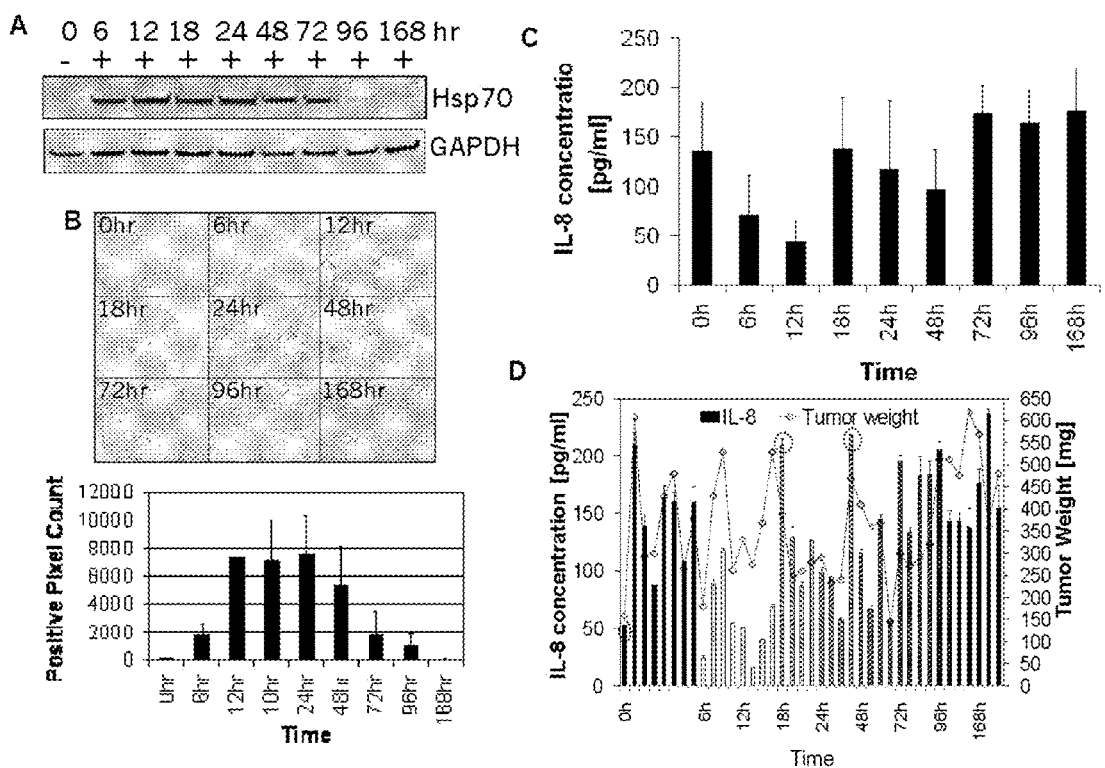
FIG. 5 Hsp70 induction observed in tumors derived from GTL-16 tumor-bearing mice treated with NVP-AUY922 by western blot analysis of total protein lysates (A) and IHC of paraffin-embedded tumors where the staining was quantified by Aperio ScanScope (B). Early drop in serum IL-8 levels (C) post-treatment with 75 mg/kg single dose of NVP-AUY922 (n=4 mice/time point, except at t=0 hr where n=8 mice). Individual IL-8 levels (D) were plotted against tumor weight highlighting mouse to mouse variance.
Figure 6:
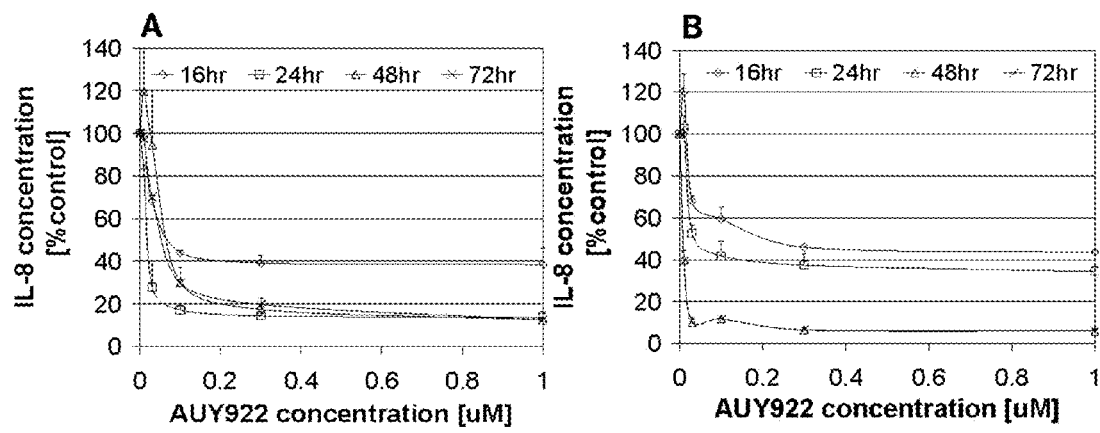
FIG. 6 Dose dependent suppression of IL-8 accumulation as measured in cell culture supernatants collected from GTL-16 (A) and A375 (B) cell lines treated with NVP-AUY922, respectively.

A significant decrease in IL-8 levels was observed in serum derived from GTL-16 tumor-bearing mice as early as 6 hr after administration of NVP-AUY922. A maximum decline of approximately 70% was reached at 12 hr post-treatment and by 72 hr; IL-8 recovers to pre-treatment levels, which is typical of a single dose regimen as shown in FIG. 5C. Mouse-to-mouse variance in serum IL-8 levels is evident in the individual sample data, where IL-8 levels and their respective tumor weights were plotted (FIG. 5D). In particular two data points at 18 hr and 24 hr appear to skew the overall IL-8 trend. IL-8 serum levels derived from A375 tumor-bearing mice dropped approximately 40% at 48 hr post-treatment with a single 60 mg/kg dose of NVP-AUY922 and recovered to their pre-treatment level at 168 hr post-treatment. The relative difference in percentage decrease in IL-8 levels between the two xenograft models can be explained by the use of different compound dosages and the different tumor environments. Murine IL-8 levels, measured indirectly as mu KC were found to be unchanged, which indicates that the decreases in human IL-8 that were measured in the serum, directly resulted from the tumor and not from any host effect. In conclusion, IL-8 accumulation in serum from tumor-bearing mice was suppressed in response to Hsp90 inhibition within the tumor environment and supports our in vitro findings in supernatants derived from GTL-16 and A375 cells.

EQUIVALENTS

Those skilled in the art will recognize, or be able to ascertain using no more than routine experimentation, many equivalents of the specific embodiments of the invention described herein. Such equivalents are intended to be encompassed by the following claims. Any combination of the embodiments disclosed in the dependent claims are contemplated to be within the scope of the invention.

INCORPORATION BY REFERENCE

The contents of all references, patents and published patent applications cited throughout this application, as well as the figures and Sequence Listing, are expressly incorporated herein by reference.

The invention claimed is:

1. A method of assessing the efficacy of a treatment regimen for treating melanoma or gastric cancer in a subject, wherein the treatment regimen comprises administration of Hsp90 inhibitor NVP-AUY922, the method comprising:
   a) contacting a first tumor sample obtained from said subject prior to administering NVP-AUY922 to the subject with an anti-IL-8 antibody to detect IL-8 protein levels;
   b) contacting a second tumor sample obtained from the same subject following administration of NVP-AUY922 with an anti-IL-8 antibody to detect IL-8 protein levels; and
   c) comparing the IL-8 protein levels from the first and second tumor samples, wherein a 40-70% decrease in the level of IL-8 detected in the second tumor sample relative to the level of IL-8 detected in the first tumor sample is an indication that the treatment regimen is efficacious for treating melanoma or gastric cancer in the subject.

* * * * *